(12) United States Patent
Yap et al.

(10) Patent No.: US 9,576,461 B2
(45) Date of Patent: Feb. 21, 2017

(54) PRIMARY TAG AND A SECONDARY TAG FOR COMMUNICATION WITH EACH OTHER, AND A SYSTEM COMPRISING A PRIMARY TAG AND ONE OR MORE SECONDARY TAGS

(71) Applicant: CADI SCIENTIFIC PTE LTD, Singapore (SG)

(72) Inventors: Kon Sang Yap, Perak (MY); Jing Feei Teh, Singapore (SG); Zenton Goh, Singapore (SG); Hon Cheong Ng, Singapore (SG)

(73) Assignee: CADI SCIENTIFIC PTE LTD, Singapore (SG)

( * ) Notice: Subject to any disclaimer, the term of this patent is extended or adjusted under 35 U.S.C. 154(b) by 446 days.

(21) Appl. No.: 14/082,229

(22) Filed: Nov. 18, 2013

(65) Prior Publication Data

US 2015/0137948 A1 May 21, 2015

(51) Int. Cl.
| | | |
|---|---|---|
| G06K 7/10 | (2006.01) | |
| G08B 21/02 | (2006.01) | |
| G06K 19/07 | (2006.01) | |
| G06F 19/00 | (2011.01) | |

(52) U.S. Cl.
CPC ....... *G08B 21/0258* (2013.01); *G06K 19/0716* (2013.01); *G06K 19/0718* (2013.01); *G06K 19/0725* (2013.01); *G06F 19/328* (2013.01)

(58) Field of Classification Search
CPC .............. G06K 7/0008; G06K 19/0723; G06K 19/07749; G06K 2017/0045; G06K 7/10366; G07C 9/00111; G08B 21/0202; G08B 21/0208; G08B 21/0227; G08B 21/02; G08B 21/0288
See application file for complete search history.

(56) References Cited

U.S. PATENT DOCUMENTS

| | | | | |
|---|---|---|---|---|
| 7,183,913 B2 * | 2/2007 | Hughes | ..................... | B63C 9/22 340/539.15 |
| 2004/0239435 A1 * | 12/2004 | Hughes | ..................... | B63C 9/22 333/1.1 |
| 2005/0073419 A1 * | 4/2005 | Gary | .................. | G08B 21/0202 340/573.1 |
| 2005/0200487 A1 * | 9/2005 | O'Donnell | ............. | A62B 99/00 340/573.1 |
| 2005/0280535 A1 * | 12/2005 | Gary | .................. | G08B 21/0211 340/572.1 |
| 2006/0071756 A1 * | 4/2006 | Steeves | .............. | G06K 7/10108 340/10.1 |
| 2007/0013521 A1 * | 1/2007 | Lindsay | ............. | G06K 19/0716 340/572.1 |
| 2010/0134257 A1 * | 6/2010 | Puleston | .............. | G06K 7/0008 340/10.4 |

(Continued)

*Primary Examiner* — Sisay Yacob
(74) *Attorney, Agent, or Firm* — Hultquist, PLLC; Steven J. Hultquist

(57) ABSTRACT

Various embodiments relate to tags, methods of using tags, systems, and methods of using systems. Various embodiments may be suitable for identifying a human or an animal. Various embodiments may provide mother-infant matching and cot-infant matching for both single and multiple births; monitoring of the location, movement, and status of the tags; detection of tampering and unauthorized removal of infant tags; and organizing of tags.

40 Claims, 10 Drawing Sheets

(56) References Cited

U.S. PATENT DOCUMENTS

2010/0278087 A1\* 11/2010 Kawakami ........ H04W 52/0216
  370/311
2010/0283584 A1\* 11/2010 McAllister ............ B65C 9/1865
  340/10.1

\* cited by examiner

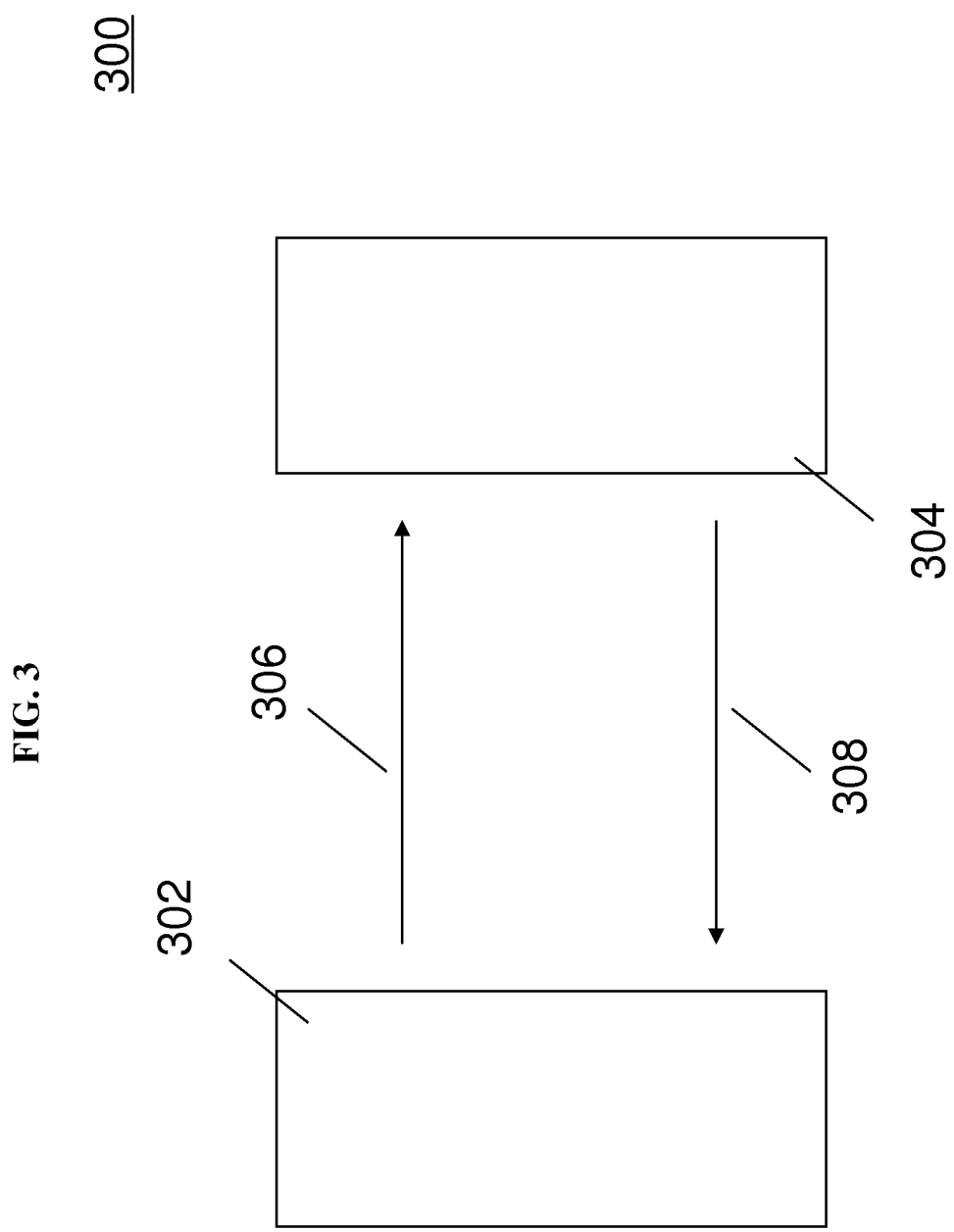

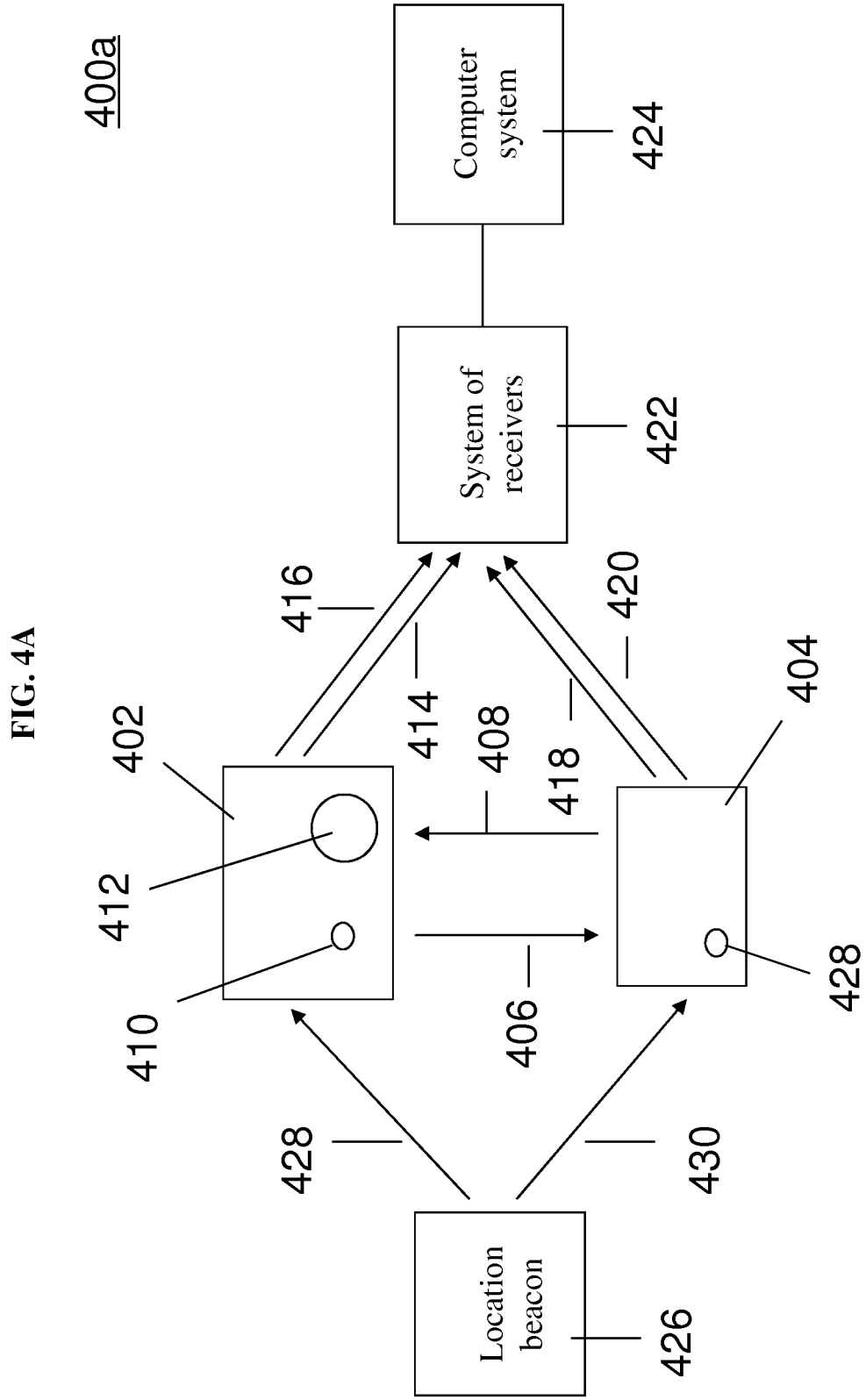

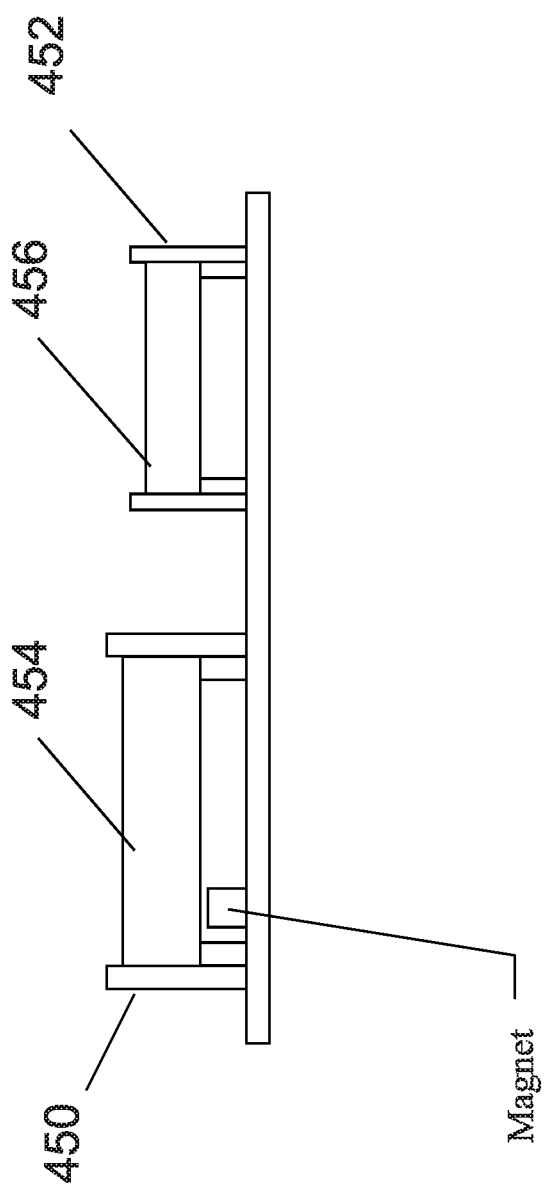

FIG. 5

500 send a first tag-to-tag signal from a primary tag to a secondary tag
502 receive the first tag-to-tag signal by the secondary tag
504 send a second tag-to-tag signal by the secondary tag, upon receiving the first tag-to-tag signal
506 receive the second tag-to-tag signal by the primary tag
508 identify the secondary tag, by the primary tag, as a correct secondary tag associated with the primary tag, if the unique secondary tag identification code in the second tag-to-tag signal matches a secondary tag identifier stored in the primary tag
510

FIG. 6

600 store a secondary tag identifier
602 receive a second tag-to-tag signal from the secondary tag
604 identify the secondary tag as a correct secondary tag associated with the primary tag if the unique secondary tag identification code in the second tag-to-tag signal matches the secondary tag identifier
606

| receive a first tag-to-tag signal from the primary tag |
|---|

702

| send a second tag-to-tag signal upon receiving the first tag-to-tag signal |
|---|

704

PRIMARY TAG AND A SECONDARY TAG FOR COMMUNICATION WITH EACH OTHER, AND A SYSTEM COMPRISING A PRIMARY TAG AND ONE OR MORE SECONDARY TAGS

TECHNICAL FIELD

Various aspects of this disclosure relate to tags, methods of using tags, systems, and methods of using systems.

BACKGROUND

Many hospitals use identification (ID) bands to match a newborn to his or her mother and to match a newborn to his or her cot. This method, being rather manual, requires the staff to be diligent in ensuring that the ID bands are correctly labeled when they are first attached to the mother, her newborn, and the cot. This manual method is prone to human error. For example, a staff, in her busyness, may misread the names or ID numbers and end up giving the wrong newborn to the mother, who, having just given birth, may not be alert enough to notice the error. Such a mismatch or mix-up can lead to a baby being breastfed by a wrong mother, and, in a worst-case scenario, can also lead to the mother going home with a wrong baby. One way to help prevent such a mismatch or mix-up is to use, in addition to the manual method, an electronic matching method that is less prone to human error. Such an electronic method will give the caregiver an additional level of confidence that the correct baby will always be given to the mother or placed in the cot intended for the baby.

SUMMARY

In various embodiments, a primary tag for communication with a secondary tag may be provided. The primary tag may include a memory circuit configured to store a secondary tag identifier. The primary tag may further include a receiver circuit configured to receive a second tag-to-tag signal from the secondary tag. The second tag-to-tag signal may include a unique secondary tag identification code. The primary tag may also include a processor circuit configured to identify the secondary tag as a correct secondary tag associated with the primary tag if the unique secondary tag identification code in the second tag-to-tag signal matches the secondary tag identifier stored in the memory circuit.

In various embodiments, a secondary tag for communication with a primary tag may be provided. The secondary tag may include a receiver circuit configured to receive a first tag-to-tag signal from the primary tag. The first tag-to-tag signal may include a unique primary tag identification code. The secondary tag may further include a first transmitter circuit configured to send a second tag-to-tag signal upon the receiver circuit receiving the first tag-to-tag signal. The second tag-to-tag signal may include a unique secondary tag identification code.

In various embodiments, a system for identifying a human or an animal may be provided. The system may include a primary tag and a secondary tag. The primary tag may be configured to send a first tag-to-tag signal. The secondary tag may be configured to receive the first tag-to-tag signal. The secondary tag may be further configured to send a second tag-to-tag signal upon receiving the first tag-to-tag signal. The second tag-to-tag signal may include a unique secondary tag identification code. The primary tag may be further configured to store a secondary tag identifier and receive the second tag-to-tag signal. The primary tag may be further configured to identify the secondary tag as a correct secondary tag associated with the primary tag if the unique secondary tag identification code in the second tag-to-tag signal matches the secondary tag identifier stored in the primary tag.

In various embodiments, a method of identifying a human or an animal may be provided. The method may include, sending a first tag-to-tag signal from a primary tag to a secondary tag. The method may include, receiving the first tag-to-tag signal by the secondary tag. The method may further include sending a second tag-to-tag signal by the secondary tag, upon receiving the first tag-to-tag signal. The second tag-to-tag signal may include a unique secondary tag identification code. The method may also include receiving the second tag-to-tag signal by the primary tag. The method may further include identifying the secondary tag, by the primary tag, as a correct secondary tag associated with the primary tag if the unique secondary tag identification code in the second tag-to-tag signal matches a secondary tag identifier stored in the primary tag.

In various embodiments, a method of controlling a primary tag for communication with a secondary tag may be provided. The method may include storing a secondary tag identifier. The method may include receiving a second tag-to-tag signal from the secondary tag. The second tag-to-tag signal may include a unique secondary tag identification code. The method may also include identifying the secondary tag as a correct secondary tag associated with the primary tag if the unique secondary tag identification code in the second tag-to-tag signal matches the secondary tag identifier.

In various embodiments, a method of controlling a secondary tag for communication with a primary tag according to various embodiments. The method may include receiving a first tag-to-tag signal from the primary tag. The first tag-to-tag signal may include a unique primary tag identification code. The method may include sending a second tag-to-tag signal upon receiving the first tag-to-tag signal. The second tag-to-tag signal may include a unique secondary tag identification code.

BRIEF DESCRIPTION OF THE DRAWINGS

The invention will be better understood with reference to the detailed description when considered in conjunction with the non-limiting examples and the accompanying drawings, in which:

FIG. 3 shows a schematic of a system for identifying a human or an animal according to various embodiments.

FIG. 4A shows a schematic of a system for identifying a human or an animal according to various embodiments.

FIG. 4B shows a schematic of a primary tag storage bracket according to various embodiments and a secondary tag storage bracket according to various embodiments.

FIG. 5 shows a schematic of a method of identifying a human or an animal according to various embodiments.

FIG. 6 shows a schematic of a method of controlling a primary tag for communication with a secondary tag according to various embodiments.

FIG. 7 shows a schematic of a method of controlling a secondary tag for communication with a primary tag according to various embodiments.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized, and structural and logical changes may be made without departing from the scope of the invention. The various embodiments are not necessarily mutually exclusive, as some embodiments can be combined with one or more other embodiments to form new embodiments.

In order that the invention may be readily understood and put into practical effect, particular embodiments will now be described by way of examples and not limitations, and with reference to the figures.

Figure 1A:
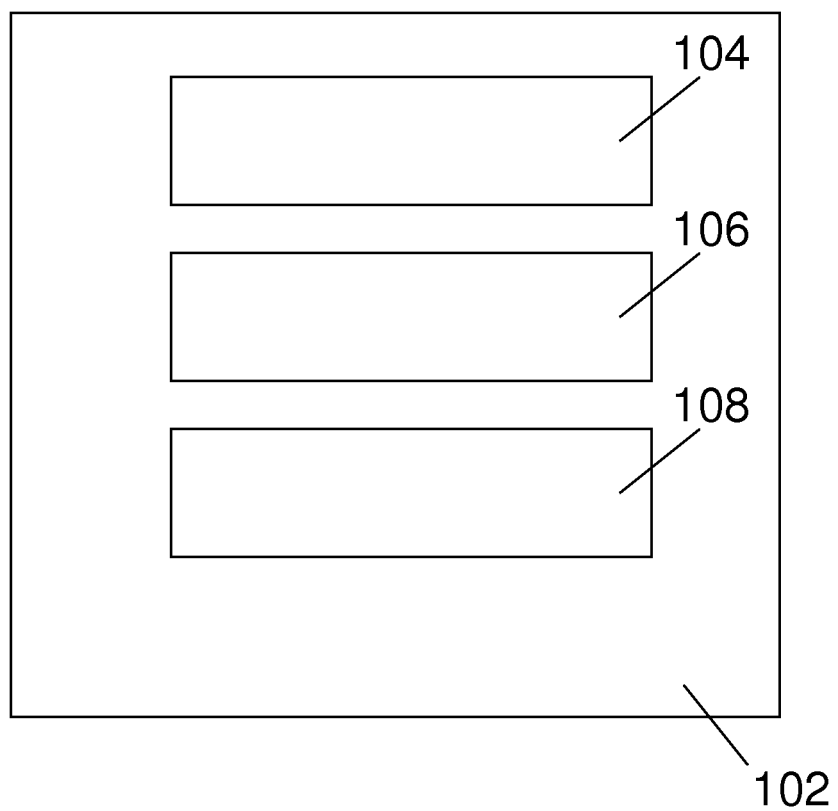
FIG. 1A shows a schematic of a primary tag according to various embodiments.

FIG. 1A shows a schematic 100a of a primary tag 102 according to various embodiments. In various embodiments, a primary tag 102 for communication with a secondary tag (not shown in FIG. 1) may be provided. The primary tag 102 may include a memory circuit 104 configured to store a secondary tag identifier. The primary tag 102 may further include a receiver circuit 106 configured to receive a second tag-to-tag signal from the secondary tag. The second tag-to-tag signal may include a unique secondary tag identification code. The primary tag 102 may also include a processor circuit 108 configured to identify the secondary tag as a correct secondary tag associated with the primary tag 102 if the unique secondary tag identification code in the second tag-to-tag signal matches the secondary tag identifier stored in the memory circuit 104.

In other words, a primary tag 102 including a memory circuit 104, a receiver circuit 106 and a processor circuit 108 may be provided. The memory circuit 104 may be configured to store a secondary tag an identifier. The receiver circuit 106 may be configured to receive a second tag-to-tag signal from a secondary tag. The second tag-to-tag signal may include a unique secondary tag identification code. The processor circuit 108 may be configured to compare the secondary tag identifier with the unique secondary tag identification code. If the secondary tag identifier matches the unique secondary tag identification code, the secondary tag may be identified as the correct secondary tag that is associated with the primary tag 102. On the other hand, if the secondary tag identifier does not match the unique secondary tag identification code, the secondary tag may be identified as an incorrect secondary tag not associated with the primary tag 102.

In various embodiments, a "circuit" may be understood as any kind of a logic implementing entity, which may be special-purpose circuitry or a processor executing software stored in a memory, firmware, or any combination thereof. Thus, in various embodiments, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program (e.g. a computer program using a virtual machine code such as Java).

The primary tag 102 may further include a first transmitter circuit configured to send a first tag-to-tag signal. The first tag-to-tag signal may include a unique primary tag identification code. In various embodiments, the first tag-to-tag signal may be transmitted to the secondary tag.

In various embodiments, the primary tag 102 may be part of an infant monitoring system. The primary tag 102 may be intended to be worn on a person, such as a mother or guardian of an infant. The primary tag 102 may in this instance be called a mother tag. Alternatively, the primary tag 102 may be intended to be attached to a bed or a cot of the infant. The primary tag 102 may in this instance be called a cot tag. The secondary tag may be worn on the infant.

In various alternate embodiments, the primary tag 102 may also be used as part of a system for monitoring people such as the elderly in a nursing home or patients in a hospital or for monitoring pets. The primary tag 102 may be worn on a caregiver such as a nurse or a owner of a pet or attached to a bed in the nursing home or the hospital. The secondary tag may be worn on an elderly person or a patient or a pet in the respective situation.

The primary tag 102 may further include a receiving portion configured to receive a detachable transmitter. The first transmitter circuit may include a built-in transmitter. The primary tag 102 may be configured to send the first tag-to-tag signal by the detachable transmitter if the detachable transmitter is attached to the primary tag 102 and configured to send the first tag-to-tag signal by the built-in transmitter if the detachable transmitter is detached from the primary tag 102.

In other words, the first transmitter circuit may be a built-in transmitter. Additionally, the primary tag 102 may further include a receiving portion. The receiving portion may be configured to receive a detachable transmitter. The primary tag 102 may be configured to send the first-tag-tag signal via the detachable transmitter when the detachable transmitter is attached to the primary tag. The built-in transmitter may be configured to stop transmitting the first-tag-to-tag signal when the detachable transmitter is attached to the primary tag. The built-in transmitter may be configured to transmit the first tag-to-tag signal when the detachable transmitter is not attached to, i.e. detached from, the primary tag 102.

Figure 1B:
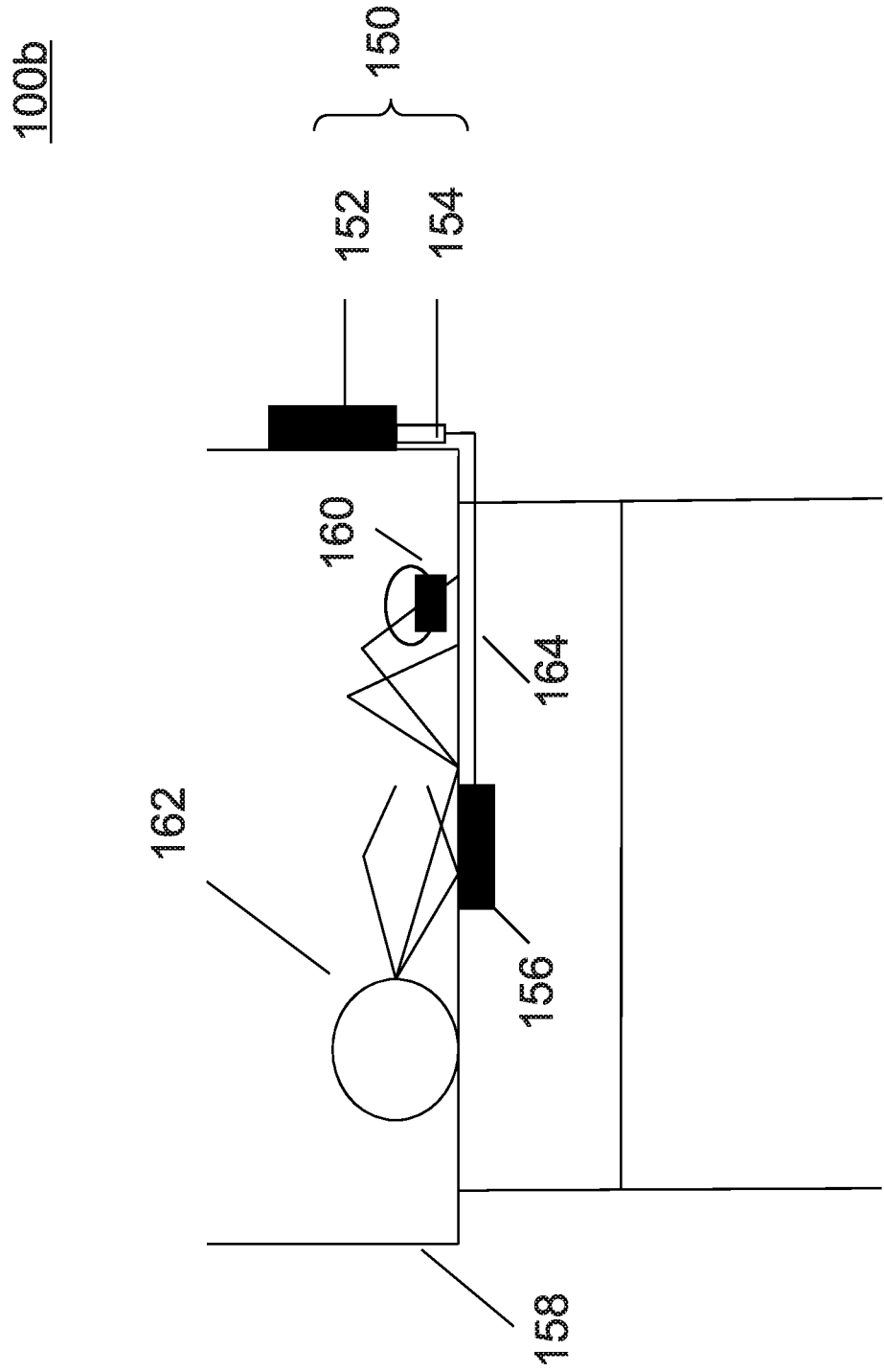
FIG. 1B shows a schematic of a primary tag, the primary tag including a built-in transmitter and a receiving portion to receive a detachable transmitter, being used according to various embodiments.

FIG. 1B shows a schematic 100b of a primary tag 150, the primary tag 150 including a built-in transmitter 152 and a receiving portion 154 to receive a detachable transmitter 156, being used according to various embodiments. The primary tag 150 may be the primary tag 102 shown in FIG. 1A. The primary tag 150 may be a cot tag and may be intended to be positioned to a cot 158 as shown in FIG. 1B. The primary tag 150 may be associated or paired with a secondary tag 160. The secondary tag 160 may be an infant tag and may be intended to be strapped to an infant 162. The detachable transmitter 156 may include a cable 164. The cable 164 may be configured to link the detachable transmitter 156 to the receiving portion 154 of the primary tag 150. The cable 164 may be received by the receiving portion 154. The primary tag 150 may be configured to send the first tag-to-tag signal by the detachable transmitter 156 if the detachable transmitter 156 is attached to the primary tag 150 and configured to send the first tag-to-tag signal by the built-in transmitter 152 if the detachable transmitter 156 is detached from the primary tag 102.

As shown in FIG. 1B, the primary tag or cot tag 150 may be placed near one end of the cot 158. If another cot happens to be placed right next to this end, the first tag-to-tag signal given by the primary tag or cot tag 150 may be received by an infant tag in the other cot. A primary tag or cot tag 150 with a detachable transmitter 156 may allow the primary tag or cot tag 150 to be placed at a desired location on the cot, e.g. near one end of the cot 158, and the detachable transmitter 156 to be placed in another location to reduce or minimize the chances of the first tag-to-tag signal being received by the infant tag in the other cot. Having a detachable transmitter 156 may allow the primary tag or cot tag 150 to be placed in the desirable location such that displays or light indicators on the primary tag or cot tag 150 remain visible to a mother or a guardian and also provides the option of placing the detachable transmitter at any location to reduce or minimize the chances of the first tag-to-tag signal, given by the primary tag 150, being received by another infant tag nearby.

For example, a mother or guardian may wish to place the primary tag or cot tag 150 at one end of the cot 158 and the detachable transmitter 156 on a cot side that is further away from a neighboring cot. As another example, a mother or guardian may wish to place the primary tag or cot tag 150 at one end of the cot 158 and the detachable transmitter 156 at the center of the bottom of the cot 158, so that when someone carrying another infant walks pass the cot 158, the distance between the infant tag on the other infant being carried and the detachable cot tag transmitter 156 on the cot 158 may be large enough to prevent the infant tag on the other infant from receiving the first tag-to-tag signals and sending response signals unnecessarily, thus helping to conserve the infant tag's battery power.

The primary tag 102 may further include a switch. The switch may be a momentary on-off switch. The first transmitter circuit may be configured to send the first tag-to-tag signal by activation (e.g. manual activation) of the switch. The switch may enable a person, such as a mother or guardian of an infant, to verify, on an on-demand basis, whether a secondary tag is a correct secondary tag associated with the primary tag. For instance, the switch enables a mother or a guardian to verify, on an on-demand basis, whether the infant the mother or the guardian is carrying is the correct infant. The switch may also enable the mother or the guardian to verify, on an on-demand basis, whether an infant in a cot is the correct baby for the cot.

The first transmitter circuit may be further configured to send the first tag-to-tag signal at preset intervals. In various embodiments, the preset intervals may be fixed intervals. In various embodiments, the preset intervals may range from 1 second to 10 seconds. In various embodiments, the preset intervals may be configurable by a tag configuration device. Other preset intervals may also be used, depending on the design, the application, and user requirements.

The primary tag 102 may further include a display circuit configured to give a first visual alert if the unique secondary tag identification code in the second tag-to-tag signal matches the secondary tag identifier stored in the memory circuit. The primary tag 102 may further include an alarm circuit configured to give additionally a first audio alert if a time lapse exceeds a preset duration, the time lapse being measured from the time at which the unique secondary tag identification code in the previous second tag-to-tag signal matches the secondary tag identifier stored in the memory circuit to the time at which the unique secondary tag identification code in the second tag-to-tag signal matches the secondary tag identifier stored in the memory circuit.

In other words, the display circuit may be configured to give the first visual alert and the alarm circuit may be configured to give the first audio alert when the unique secondary tag identification code in the second tag-to-tag signal matches the secondary tag identifier stored in the memory circuit if the time lapse exceeds the preset duration. The display circuit may be configured to give the first visual alert while the alarm circuit may be configured not to give the first audio alert when the unique secondary tag identification code in the second tag-to-tag signal matches the secondary tag identifier stored in the memory circuit if the time lapse is within the preset duration.

For avoidance of doubt, the condition in which the time lapse exceeds the preset duration includes the first time at which the unique secondary tag identification code in the second tag-to-tag signal matches the secondary tag identifier stored in the memory circuit. For the first time at which the unique secondary tag identification code in the second tag-to-tag signal matches the secondary tag identifier stored in the memory circuit, there is no previous second-tag-to-tag signal including the unique secondary tag identification code to be matched with the secondary tag identifier stored in the memory circuit and the time lapse in such an instance may be taken to be infinity.

The primary tag 102 may further include a second transmitter circuit. The second transmitter circuit may be configured to send a matching information signal if the unique secondary tag identification code in the second tag-to-tag signal matches the secondary tag identifier stored in the memory circuit and if a time lapse exceeds a preset duration, the time lapse being measured from the time at which the unique secondary tag identification code in the previous second tag-to-tag signal matches the secondary tag identifier stored in the memory circuit to the time at which the unique secondary tag identification code in the second tag-to-tag signal matches the secondary tag identifier stored in the memory circuit. The matching information signal may include the unique primary tag identification code and other information including the location and battery level of the primary tag. The matching information signal may additionally or alternatively include an indication that the unique secondary tag identification code in the second tag-to-tag signal matches the secondary tag identifier stored in the memory circuit.

For avoidance of doubt, the condition in which the time lapse exceed the preset duration includes the first time at which the unique secondary tag identification code in the second tag-to-tag signal matches the secondary tag identifier stored in the memory circuit.

In various embodiments, the preset time lapse may be configurable by a tag configuration device. In various embodiments, the preset time lapse may range from 10 seconds to 10 minutes. Other preset time lapses may also be used, depending on the design, the application, and user requirements.

In various embodiments, the first transmitter circuit and the second transmitter circuit are separate circuits. In various alternate embodiments, the first transmitter circuit and the second transmitter circuit are the same circuit or part of the same circuit.

In various embodiments, the alarm circuit may be further configured to give a second audio alert and the display circuit may be further configured to give a second visual alert if the unique secondary tag identification code in the second tag-to-tag signal does not match the secondary tag identifier stored in the memory circuit. In other words, both the second audio alert and the second visual alert may be given if the unique secondary tag identification code in the second tag-to-tag signal does not match the secondary tag identifier stored in the memory circuit. The second audio alert may be different from the first audio alert. Also, the second visual alert may be different from the first visual alert.

In various embodiments, the first audio alert may be a first melody. In various embodiments, the first visual alert may be a green blinking light. In various embodiments, the second audio alert may be a second melody. In various embodiments, the second visual alert may be a red blinking light.

The second transmitter circuit may be further configured to send a mismatch information signal if the unique secondary tag identification code in the second tag-to-tag signal does not match the secondary tag identifier stored in the memory circuit. The mismatch information signal may include information indicating a mismatch. In other words, the mismatch information signal may include information indicating that the unique secondary tag identification code in the second tag-to-tag signal does not match the secondary tag identifier stored in the memory circuit.

The first tag-to-tag signal may be a short range signal. The second tag-to-tag signal may also be a short range signal.

In various embodiments, a transmission range of the first tag-to-tag signal may be configurable by a tag configuration device. Also, in various embodiments, a reception range of the second tag-to-tag signal may be configurable by the tag configuration device.

In various embodiments, the first transmitter circuit may be configured to send the first tag-to-tag signal having a first maximum transmission range when the primary tag 102 is intended to be worn on a person and configured to send the first tag-to-tag signal having a second maximum transmission range when the primary tag 102 is intended to be attached to a cot.

In various embodiments, the receiving circuit may be configured to receive the second tag-to-tag signal having a first maximum reception range when the primary tag is intended to be worn on a person and configured to receive the second tag-to-tag signal having a second maximum reception range when the primary tag 102 is to intended be attached to a cot. The first maximum transmission range may be longer than the second maximum transmission range. The first maximum reception range may be longer than the second maximum reception range. In other words, the maximum reception range and/or the maximum transmission range of the primary tag in a cot-infant tag system may be shorter than in a mother-infant tag system. A shorter reception range and/or shorter transmission range may help to reduce the chances of cot tag signals and infant tag signals crossing from one cot to another. This may be advantageous in a setting such as a maternity ward, as cots in a maternity ward may be placed right next to each other.

In various embodiments, the first maximum transmission range may be about 40 cm. In various embodiments, the first maximum reception range may be about 40 cm. In various embodiments, the second maximum transmission range may be about 36 cm. In various embodiments, the second maximum reception range may be about 36 cm.

In various embodiments, the first tag-to-tag signal may be a low radio frequency signal. The first tag-to-tag signal may have a frequency ranging from 125 kHz to 134 kHz. In various first tag-to-tag embodiments, the second tag-to-tag signal may be a low frequency signal. The second tag-to-tag signal may have a frequency in the range of 125 kHz to 134 kHz. However, the first tag-to-tag signal and the second tag-to-tag signal may have frequencies that fall outside of 125 kHz to 134 kHz. The frequencies of the first tag-to-tag signal and the second tag-to-tag signal may be subjected to the frequency allocation rules in which the primary tags and the secondary tags are used.

In various embodiments, the matching information signal may be a long range signal. The mismatch information signal may also be a long range signal. In various embodiments, a transmission range of the matching information signal may be configurable by a tag configuration device. Also, in various embodiments, a transmission range of the mismatch information signal may be configurable by the tag configuration device. In various embodiments, the matching information signal may have a transmission range of 10 m to 25 m. The mismatch information signal may also have a transmission range 10 m to 25 m. Other ranges may also be used, depending on the design, the application, and user requirements.

In various embodiments, the matching information signal may be an ultrahigh radio frequency signal. The matching information signal may have a frequency in the range of 868 MHz to 928 MHz. In various embodiments, the mismatch information signal may be an ultrahigh radio frequency signal. The mismatch information signal may have a frequency in the range of 868 MHz to 928 MHz. However, the matching information signal and the mismatch information signal may have frequencies that fall outside of 868 MHz to 928 MHz. The frequencies of the matching information signal and the mismatch information signal may be subjected to the frequency allocation rules in which the primary tags and the secondary tags are used.

In various embodiments, the matching information signal and the mismatch information signal may be configured to be received by at least one receiver connected to a computer system. In various embodiments, the information comprised in the matching information signal and the mismatch information signal may be configured to be received, stored, and processed by the computer system. The at least one receiver and the computer system may form part of a location and status tracking system. The location and status tracking system may be part of a hospital's nurse call system or a security system.

In various embodiments, the primary tag 102 may include a second transmitter circuit. The receiver circuit may be configured to receive a beacon signal from a location beacon. The second transmitter circuit may be configured to send a primary tag response information signal in response to the beacon signal received by the receiver circuit. The primary tag response information signal may include information indicating the location of the primary tag 102. The location beacon may be installed in a room to provide a room location for the primary tag 102. The location beacon may additionally or alternatively be installed at strategic exit locations to provide the location of the exit locations for the purpose of detecting infant abduction or unauthorized movement of infants.

In various embodiments, the primary tag 102 may include a second transmitter circuit. The second transmitter circuit may be configured to send an information signal. The information signal may include the unique primary tag identification code and other information including the location and battery level of the primary tag 102. The information signal may be different from the matching information signal and the mismatch information signal.

In various embodiments, at least one parameter of the primary tag 102 is configured by a tag configuration device, the at least one parameter being selected from a group including the intervals at which the first tag-to-tag signal is sent and a transmission range of the first tag-to-tag signal.

In various embodiments, the unique secondary tag identification code in the second tag-to-tag signal may match the secondary tag identifier stored in the memory circuit if the unique secondary tag identification code and the secondary tag identifier include a common string of characters. Accordingly, the unique secondary tag identification code in the second tag-to-tag signal may not match the secondary tag identifier stored in the memory circuit if the unique secondary tag identification code and the secondary tag identifier do not include a common string of characters. In various instances, the unique secondary tag identification code in the second tag-to-tag signal may match the secondary tag identifier stored in the memory circuit if the unique secondary tag identification code and the secondary tag identifier include a minimum number of characters that are common. The minimum number of characters may be predefined. In various instances, the unique secondary tag identification code in the second tag-to-tag signal may match the secondary tag identifier stored in the memory circuit if the characters in predefined positions in a string of characters are the same.

In various other embodiments, the unique secondary tag identification code in the second tag-to-tag signal may match the secondary tag identifier stored in the memory circuit if the unique secondary tag identification code and the secondary tag identifier are the same. Accordingly, the unique secondary tag identification code in the second tag-to-tag signal may not match the secondary tag identifier stored in the memory circuit if the unique secondary tag identification code and the secondary tag identifier are different.

In various alternate embodiments, the unique secondary tag identification code in the second tag-to-tag signal may match the secondary tag identifier stored in the memory circuit if the unique secondary tag identification code and the secondary tag identification satisfy a predetermined condition or satisfy a predetermined relation. For instance, the primary tag 102 may be configured such the unique secondary tag identification code in the second tag-to-tag signal matches the secondary tag identifier stored in the memory circuit if the last four digits of the unique secondary tag identification code and the last four digits of the secondary tag identifier add up to a predefined number, e.g. 10,000. In another instance, the primary tag 102 may be configured such that the secondary tag identifier stored in the memory circuit is linked with one or more predetermined secondary tag identification codes and a unique secondary tag identification code in the second tag-to-tag signal may match the secondary tag identifier only if the unique secondary tag identification code is one of the one or more predetermined secondary tag identification codes. Accordingly, the unique secondary tag identification code in the second tag-to-tag signal may not match the secondary tag identifier stored in the memory circuit if the unique secondary tag identification code and the secondary tag identification does not satisfy the predetermined condition or does not satisfy a predetermined relation.

In various embodiments, a primary tag 102 and one or more secondary tags may be paired at the manufacturer's end. In various other embodiments, a primary tag 102 and one or more secondary tags may be paired at the user's end. In the current context, pairing may mean associating one or more secondary tags with a primary tag. Pairing may include storing the secondary tag identifiers of the one or more secondary tags in the primary tag such that when the primary tag 102 receives a second tag-to-tag signal from a paired secondary tag, the processor circuit 108 of the primary tag 102 identifies the paired secondary tag as a correct secondary tag associated with the primary tag 102 if the unique secondary tag identification code in the second tag-to-tag signal matches the secondary tag identifier stored in the memory circuit 104. Pairing of the primary tag 102 and the one or more secondary tags at the manufacturer's end may have the advantages that the primary tag 102 and the one or more secondary tags are already pre-matched or pre-paired and ready for use when they reach the user, freeing the user of the need to match or pair the tags before use.

In various embodiments, the primary tag 102 may be labeled with the unique primary tag identification code such that the unique primary tag identification code is visually recognizable and readable. Labeling the primary tag 102 with the unique primary tag identification code may provide a means for a person to visually check whether the primary tag 102 to be used or organized is the correct primary tag.

In various embodiments, the primary tag 102 may be configured to be stored in a primary storage bracket. The primary tag's capability to send or receive any signal may be turned off by the primary storage bracket after the primary tag 102 is placed in the primary tag storage bracket for a preset period. Turning off the primary tag's capability to send or receive any signal, when the primary tag 102 is not being used, may help to conserve the battery power of the primary tag 102. The preset period may be useful in that any accidental or unintentional placement of the primary tag 102 in the primary tag bracket for a period shorter than the preset period will not turn off the tag's capability to send or receive any signal. The preset period may be configurable by a tag configuration device. The preset period may range from 1 second to 10 seconds. Other ranges may be used, depending on the design, the application, and user requirements.

In various embodiments, the memory circuit 104 may be configured to store a plurality of secondary tag identifiers. The processor circuit may be configured to identify a secondary tag as a correct secondary tag associated with the primary tag if the unique secondary tag identification code in the second tag-to-tag signal matches any one of the secondary tag identifiers stored in the memory circuit. In other words, a primary tag 102 may be paired or associated with one or more secondary tags. Pairing or associating a primary tag 102 with one or more secondary tags may be useful such as when a mother gives birth to multiple babies. The mother may carry one mother tag while each baby has an infant tag associated or paired with the mother tag.

Figure 2A:
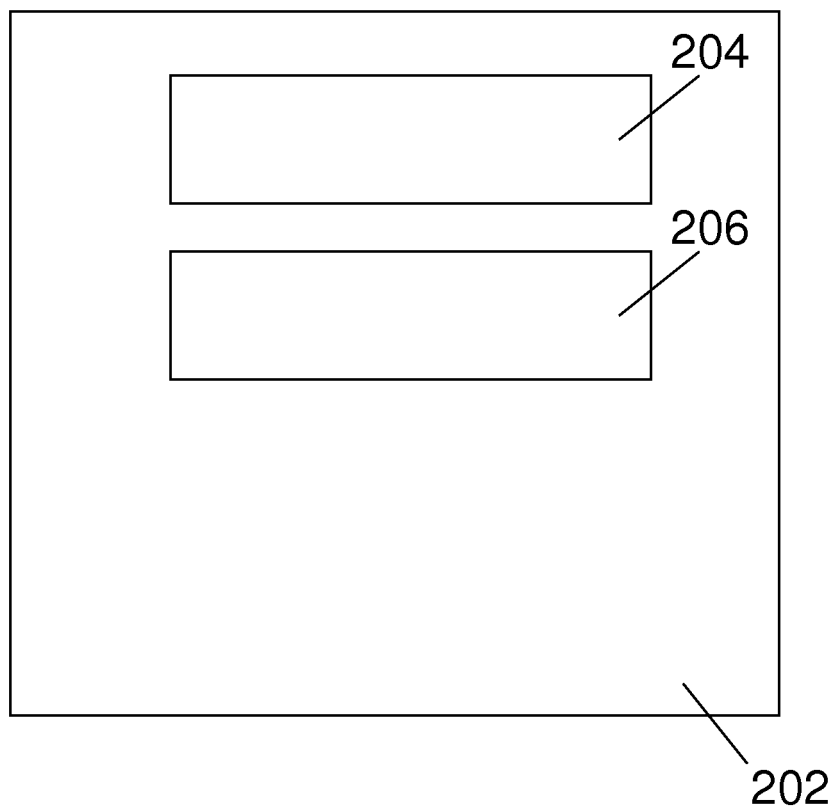
FIG. 2A shows a schematic of a secondary tag according to various embodiments.

FIG. 2A shows a schematic 200a of a secondary tag 202 according to various embodiments. In various embodiments, a secondary tag 202 for communication with a primary tag (not shown in FIG. 2) may be provided. The secondary tag 202 may include a receiver circuit 204 configured to receive a first tag-to-tag signal from the primary tag. The first tag-to-tag signal may include a unique primary tag identification code. The secondary tag may further include a first transmitter circuit 206 configured to send a second tag-to-tag signal upon the receiver circuit 204 receiving the first tag-to-tag signal. The second tag-to-tag signal may include a unique secondary tag identification code.

In other words, a secondary tag 202 including a receiver circuit 204 and a first transmitter circuit 206 may be provided. The receiver circuit 204 may be configured to receive a first tag-to-tag signal from the primary tag. The first tag-to-tag signal may include a unique primary tag identification code. The first transmitter circuit 206 may be configured to send a second tag-to-tag signal upon the receiver circuit 204 receiving the first tag-to-tag signal. The second tag-to-tag signal may include a unique secondary tag identification code.

The secondary tag 202 may further include a skin side configured to be positioned over the skin of a human or an animal. The secondary tag 202 may further include a skin detection circuit configured to detect whether the skin side is within a predetermined distance from the skin of a human or an animal. The first transmitter circuit 206 may be further configured to send the second tag-to-tag signal upon the receiver circuit 204 receiving the first tag-to-tag signal if the skin detection circuit determines that the skin side of the secondary tag 202 is within a predetermined distance from the skin of a human or an animal. The skin-sensing capability may be intended to provide an indication of whether the secondary tag (or infant tag) is adequately secured to a person such as an infant or an animal. In various embodiments, the skin detection circuit may be configured to detect whether the skin side is within a predetermined distance using infrared radiation. In various other embodiments, the skin detection circuit may be configured to detect whether the skin side is within a predetermined distance using capacitive or magnetic proximity sensing technologies or any other types of sensing technologies.

In various embodiments, the secondary tag 202 may be part of an infant monitoring system. The secondary tag 202 may be intended to be worn on a person such as an infant. The secondary tag 202 may be called an infant tag.

In various alternate embodiments, the secondary tag 202 may also be used as part of a system for monitoring people such as the elderly in a nursing home or patients in a hospital or for monitoring pets. The secondary tag 202 may for instance be worn on an elderly person in the nursing home, a patient in a hospital or a pet.

The secondary tag 202 may further include a memory circuit configured to store a primary tag identifier. The secondary tag 202 may also include a processor circuit configured to identify a primary tag as a correct primary tag associated with the secondary tag if the unique primary tag identification code matches the primary tag identifier stored in the memory circuit. Storing the primary tag identifier may provide an option for the secondary tag 202 to use the primary tag identifier for deciding how to respond to the primary tag when the secondary tag receives the first tag-to-tag signal. For example, the secondary tag 202 may be configured in such a way that if, within a short period, the secondary tag 202 repeatedly receives first tag-to-tag signals from the same associated primary tag (identified by comparing and matching the primary tag identifier with the unique primary tag identification code in the first tag-to-tag signals), the secondary tag 202 may not respond to every first tag-to-tag signal but may respond only selectively, for example, at predetermined intervals or after every predetermined number of times the secondary tag 202 receives the first tag-to-tag signal from the associated primary tag, to conserve the battery power of the secondary tag 202.

The secondary tag 202 may include two opposing electrical terminals. The secondary tag 202 may further include an electrically conductive strap configured to electrically connect the two opposing electrical terminals. The secondary tag 202 may also include a detection circuit configured to detect whether the two opposing electrical terminals are electrically connected by the electrically conductive strap. The first transmitter circuit 206 may be configured to send the second tag-to-tag signal upon the receiver circuit 204 receiving the first tag-to-tag signal if the detection circuit determines that the two opposing electrical terminals are electrically connected. Accordingly, the first transmitter circuit 206 may be configured not to send the second tag-to-tag signal upon the receiver circuit 204 receiving the first tag-to-tag signal if the detection circuit determines that the two opposing electrical terminals are not electrically connected (or electrically disconnected).

Figure 2B:
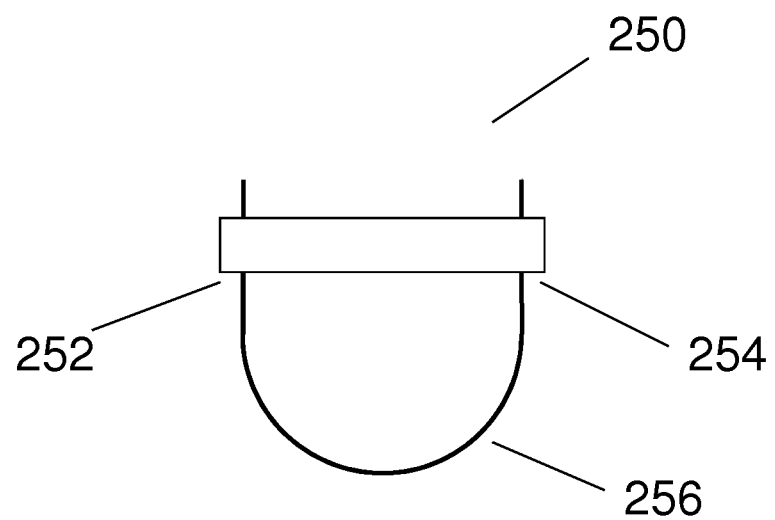
FIG. 2B shows a schematic of a secondary tag having a first electrical terminal, a second electrical terminal opposite the first electrical terminal, as well as an electrically conductive strap according to various embodiments.

FIG. 2B shows a schematic of a secondary tag 250 having a first electrical terminal 252, a second electrical terminal 254 opposite the first electrical terminal 252, as well as an electrically conductive strap 256 according to various embodiments. The secondary tag 250 may be the secondary tag 202 shown in FIG. 2A. The electrically conductive strap 256 may be configured to electrically connect the first electrical terminal 252 and the second electrical terminal 254. For instance, the electrical strap 256 may be fixed to the first electrical terminal 252. The electrical strap 256 may be releasably attached to the second electrical terminal 254. When the electrical strap 256 is attached to the second electrical terminal 254, the first electrical terminal 252 and the second electrical terminal 254 may be in electrical connection. Conversely, when the electrical strap 256 is detached from the second electrical terminal 254, the first electrical terminal 252 and the second electrical terminal 254 may not be electrically connected. In another instance, the electrical strap 256 may include a first portion and a second portion. The first portion may be attached to the first electrical terminal 252. The second portion may be attached to the second electrical terminal 254. The first electrical terminal 252 and the second electrical terminal 254 may be in electrical connection when the first portion is joined or coupled to the second portion. The first electrical terminal 252 and the second electrical terminal 254 may not be electrically connected when the first portion is not joined or not coupled to the second portion.

In various embodiments, the secondary tag 202 may further include a second transmitter circuit. The secondary tag 202 may also include two opposing electrical terminals. The secondary tag 202 may additionally include an electrically conductive strap configured to electrically connect the two opposing electrical terminals. The secondary tag 202 may also include a detection circuit configured to detect whether the two opposing electrical terminals are electrically connected by the electrically conductive strap. The second transmitter circuit may be configured to send a connection information signal if the detection circuit determines that the two opposing electrical terminals are electrically connected. Accordingly, the second transmitter circuit may be configured not to send the connection information signal if the detection circuit determines that the two opposing electrical terminals are not electrically connected (or electrically disconnected). The connection information signal may include the unique secondary tag identification code and other information including the location and battery level of the secondary tag. In various embodiments, the connection information signal may include information indicating that the two opposing electrical terminals are electrically connected by the electrically conductive strap.

The electrical conductive strap may have an electrical resistance that varies as the strap is stretched. The electrical resistance of the strap may be changed due to tampering of the strap. The secondary tag may be configured to send an information signal, such as the connection information signal, that includes information indicating that the strap may have been or might have been tampered with when the change in electrical resistance exceeds a preset threshold.

In various embodiments, the secondary tag may be configured to send the connection information signal at preset intervals.

In various embodiments, the secondary tag 202 may further include a second transmitter circuit. The secondary tag 202 may also include two opposing electrical terminals. The secondary tag 202 may additionally include an electrically conductive strap configured to electrically connect the two opposing electrical terminals. The secondary tag 202 may also include a detection circuit configured to detect whether the two opposing electrical terminals are electrically connected by the electrically conductive strap. The second transmitter circuit may be configured to send a disconnection information signal if the detection circuit determines that the two opposing electrical terminals are electrically disconnected. Accordingly, the second transmitter circuit may be configured not to send a disconnection information signal if the detection circuit determines that the two opposing electrical terminals are electrically connected. The second transmitter circuit may be configured to send the disconnection information signal at preset intervals for a preset surveillance period after the detection circuit determines that the two opposing electrical terminals are electrically disconnected. The disconnection information signal may include information indicating the strap has been severed. The second transmitter may be further configured to send a first disconnection information signal immediately after the strap is severed.

Having a preset surveillance period in which the disconnection signal is sent may limit the period in which the secondary tag 202 is active after the strap is severed, so as to conserve the battery power of the secondary tag 202.

In various embodiments, the preset intervals and/or the preset surveillance period may be configurable by a tag configuration device. The preset intervals may range from 5 seconds to 1 minute. The preset surveillance period may range from 1 minute to 10 minutes. Other ranges may be used, depending on the design, the application, and user requirements.

In various embodiments, the first transmitter circuit may be configured to send the second tag-to-tag signal upon the receiver circuit receiving the first tag-to-tag signal if the processor circuit determines that a time lapse exceeds a preset duration, the time lapse being measured from the time at which the unique primary tag identification code in the previous first tag-to-tag signal matches the primary tag identifier stored in the memory circuit to the time at which the unique primary tag identification code in the first tag-to-tag signal matches the primary tag identifier stored in the memory circuit.

For avoidance of doubt, the condition in which the time lapse exceed the preset duration includes the first time at which the unique primary tag identification code in the first tag-to-tag signal matches the primary tag identifier stored in the memory circuit. For the first time at which the unique primary tag identification code in the first tag-to-tag signal matches the primary tag identifier stored in the memory circuit, there is no previous primary tag-to-tag signal including the unique primary tag identification code to be matched with the primary tag identifier stored in the memory circuit and the time lapse in such an instance may be taken to be infinity.

The secondary tag 202 may not always respond with a second tag-to-tag signal for every matching first tag-to-tag signal the secondary tag 202 receives. For instance in a cot-infant system, it may not be required or desirable for the cot tag (i.e. the primary tag) to keep giving audio or visual alerts, considering that an infant is likely to stay in the cot for extended periods. Having the secondary tag 202 configured to send the second tag-to-tag signal upon the secondary tag 202 receiving the first tag-to-tag signal if a time lapse exceeds a preset duration may help conserve the battery power of both the primary tag/cot tag and the secondary tag/infant tag 202. The secondary tag/infant tag 202 may be configured to send the second tag-to-tag signal consecutively for multiple times, e.g. two or three times, and not just once, to reduce the chances of the primary tag/cot tag not receiving the second tag-to-tag signal because of temporary physical obstacles between the primary/cot tag and the secondary/infant tag 202.

In various embodiments, the preset time duration may range from 10 seconds to 10 minutes. Other ranges may be used, depending on the design, the application, and user requirements.

In various embodiments, a transmission range of the second tag-to-tag signal may be configurable by a tag configuration device. Also, in various embodiments, a reception range of the first tag-to-tag signal may be configurable by the tag configuration device.

In various embodiments, the first tag-to-tag signal may be a low radio frequency signal. The first tag-to-tag signal may have a frequency ranging from 125 kHz to 134 kHz. In various first tag-to-tag embodiments, the second tag-to-tag signal may be a low frequency signal. The second tag-to-tag signal may have a frequency in the range of 125 kHz to 134 kHz. However, the first tag-to-tag signal and the second tag-to-tag signal may have frequencies that fall outside of 125 kHz to 134 kHz. The frequencies of the first tag-to-tag signal and the second tag-to-tag signal may be subjected to the frequency allocation rules in which the primary tags and the secondary tags are used.

In various embodiments, the connection information signal may be a long range signal. The disconnection information signal may also be a long range signal. In various embodiments, a transmission range of the connection information signal may be configurable by a tag configuration device. Also, in various embodiments, a transmission range of the disconnection information signal may be configurable by the tag configuration device. In various embodiments, the connection information signal may have a transmission range of 10 m to 25 m. The disconnection information signal may also have a transmission range 10 m to 25 m. Other ranges may also be used, depending on the design, the application, and user requirements.

In various embodiments, the connection information signal may be an ultrahigh radio frequency signal. The connection information signal may have a frequency in the range of 868 MHz to 928 MHz. In various embodiments, the disconnection information signal may be an ultrahigh radio frequency signal. The disconnection information signal may have a frequency in the range of 868 MHz to 928 MHz. However, the connection information signal and the disconnection information signal may have frequencies that fall outside of 868 MHz to 928 MHz. The frequencies of the connection information signal and the disconnection information signal may be subjected to the frequency allocation rules in which the primary tags and the secondary tags are used.

In various embodiments, a transmission range of the connection information signal may be configurable by a tag configuration device. In various embodiments, a transmission range of the disconnection information signal may be configurable by a tag configuration device.

In various embodiments, the connection information signal may be configured to be received by at least one receiver connected to a computer system. Information comprised in the connection information signal may be configured to be received, stored, and processed by the computer system. The at least one receiver and the computer system may form part of a location and status tracking system. The location and status tracking system may be part of a hospital's nurse call system or a security system.

In various embodiments, an alert may be issued by the computer system if the computer system does not receive the connection information signal for a preset nondetection period.

In various embodiments, the disconnection information signal may be configured to be received by at least one receiver connected to a computer system. Information comprised in the disconnection information signal may be configured to be received, stored, and processed by the computer system.

In various embodiments, an alert may be issued by the computer system if the computer system does not receive the disconnection information signal for a preset nondetection period.

In various instances, issuing an alert when the computer does not receive the connection information signal and/or disconnection information signal may be used to trigger personnel, such as hospital staff, to check the secondary tag that is supposed to send the connection information signal and/or disconnection information signal, as well as the wearer of the tag. The at least one receiver and the computer system may form part of a location and status tracking system. The location and status tracking system may be part of a hospital's nurse call system or a security system.

For instance, the at least one receiver may be installed in strategic exit locations. The at least one receiver may be configured to monitor the movement of a secondary tag or an infant tag for the purpose of detecting infant abduction or unauthorized movement of infants. The at least one receiver may be configured to give an audible alarm or a visual alarm or both the audible alarm and the visual alarm when they receive a connection information signal and/or a disconnection information signal.

In various embodiments, the preset nondetection period may be configurable. Configuration of the preset nondetection period may be accomplished through application software of the computer system. The preset non detection period may range from 10 seconds to 10 minutes. Other ranges may be used, depending on the design, the application, and user requirements.

In various embodiments, the secondary tag 202 may include a second transmitter circuit. The receiver circuit 204 may be configured to receive a beacon signal from a location beacon. The second transmitter circuit may be configured to send a secondary tag response information signal in response to the receiver circuit 204 receiving the beacon signal received by the receiver circuit 204. The secondary tag response information signal may include information indicating the location of the secondary tag 202. The location beacon may be installed in a room to provide a room location for the secondary tag 202. The location beacon may additionally or alternatively be installed at strategic exit locations to provide the location of the exit locations for purpose of detecting infant abduction or unauthorized movement of infants.

In various embodiments, the secondary tag 202 may include a second transmitter circuit. The second transmitter circuit may be configured to send an information signal. The information signal may include the unique secondary tag identification code and other information including the location and battery level of the secondary tag. The information signal may be different from the connection information signal and the disconnection information signal.

In various embodiments, at least one parameter of the secondary tag 202 may be configured by a tag configuration device. The at least one parameter may be selected from a group including the intervals at which the second tag-to-tag signal is sent and a transmission range of the second tag-to-tag signal.

In various embodiments, the unique primary tag identification code in the first tag-to-tag signal may match the primary tag identifier stored in the memory circuit if the unique primary tag identification code and the primary tag identifier include a common string of characters. Accordingly, the unique primary tag identification code in the first tag-to-tag signal may not match the primary tag identifier stored in the memory circuit if the unique primary tag identification code and the primary tag identifier do not include a common string of characters. In various instances, the unique primary tag identification code in the first tag-to-tag signal may match the primary tag identifier stored in the memory circuit if the unique primary tag identification code and the primary tag identifier include a minimum number of characters that are common. The minimum number of characters may be predefined. In various instances, the unique primary tag identification code in the first tag-to-tag signal may match the primary tag identifier stored in the memory circuit if the characters in predefined positions in a string of characters are the same.

In various other embodiments, the unique primary tag identification code in the first tag-to-tag signal may match the primary tag identifier stored in the memory circuit if the unique primary tag identification code and the primary tag identifier are the same. Accordingly, the unique primary tag identification code in the first tag-to-tag signal may not match the primary tag identifier stored in the memory circuit if the unique primary tag identification code and the primary tag identifier are different.

In various alternate embodiments, the unique primary tag identification code in the first tag-to-tag signal may match the primary tag identifier stored in the memory circuit if the unique primary tag identification code and the primary tag identification satisfy a predetermined condition or satisfy a predetermined relation. For instance, the secondary tag 202 may be configured such the unique primary tag identification code in the first tag-to-tag signal matches the primary tag identifier stored in the memory circuit if the last four digits of the unique primary tag identification code and the last four digits of the primary tag identifier add up to a predefined number, e.g. 10,000. In another instance, the secondary tag 202 may be configured such that the primary tag identifier stored in the memory circuit is linked with one or more predetermined primary tag identification codes and a unique primary tag identification code in the first tag-to-tag signal may match the primary tag identifier only if the unique primary tag identification code is one of the one or more predetermined primary tag identification codes. Accordingly, the unique primary tag identification code in the first tag-to-tag signal may not match the primary tag identifier stored in the memory circuit if the unique primary tag identification code and the primary tag identification do not satisfy the predetermined condition or do not satisfy a predetermined relation.

In various embodiments, a secondary tag 202 may be paired with a primary tag at the manufacturer's end. In various other embodiments, a secondary tag 202 and a primary tag may be paired at the user's end. In the current context, pairing may mean associating one or more secondary tags with a primary tag. Pairing may include storing the primary tag identifiers of a primary tag in the secondary tag such that when the second tag 202 receives a first tag-to-tag signal from a paired primary tag, the processor circuit of the secondary tag 202 identifies the paired primary tag as a correct primary tag associated with the secondary tag 202 as the unique primary tag identification code in the first tag-to-tag signal matches the primary tag identifier stored in the memory circuit.

In various embodiments, the secondary tag may be labeled with the unique secondary tag identification code such that the unique secondary tag identification code is visually recognizable and readable. Labeling the secondary tag 202 with the unique secondary tag identification code may provide a means for a person to visually check whether the secondary tag 202 to be used or organized is the correct secondary tag.

In various embodiments, the secondary tag 202 may include a second transmitter circuit. The second transmitter circuit may be configured to send an information signal if the skin detection circuit detects that the skin side of the secondary tag is within a predetermined distance from the skin. For example, when a secondary tag/infant tag is strapped to an infant for extended periods of time, the strap may become too tight for the infant as the infant grows or becomes too loose if the infant loses weight. Having the second transmitter circuit configured to send the information signal if the skin detection circuit detects that the skin side of the secondary tag is within the predetermined distance from the skin may circumvent the problem of the strap being too tight or too loose for the infant.

In various embodiments, the secondary tag 202 may be configured to be stored in a secondary tag bracket.

FIG. 3 shows a schematic 300 of a system for identifying a human or an animal according to various embodiments. The system may include a primary tag 302 and a secondary tag 304. The primary tag 302 may be configured to send a first tag-to-tag signal 306. The secondary tag 304 may be configured to receive the first tag-to-tag signal 306. The secondary tag 304 may be further configured to send a second tag-to-tag signal 308 upon receiving the first tag-to-tag signal 306. The second tag-to-tag signal 308 may include a unique secondary tag identification code. The primary tag 302 may be further configured to store a secondary tag identifier and receive the second tag-to-tag signal 308. The primary tag 302 may be further configured to identify the secondary tag 304 as a correct secondary tag associated with the primary tag 302 if the unique secondary tag identification code in the second tag-to-tag signal 308 matches the secondary tag identifier stored in the primary tag 302.

In other words, the system may include a primary tag 302 and a secondary tag 304. The primary tag 302 may be configured to transmit a first tag-to-tag signal 306 to the secondary tag 304. The secondary tag 304 may be configured to send a second tag-to-tag signal 308 after receiving the first tag-to-tag signal 306. The primary tag 302 may be configured to store a secondary tag identifier. After receiving the second tag-to-tag signal 308, the primary tag 302 may be configured to compare the unique secondary tag identification code in the second tag-to-tag signal 308 with the secondary tag identifier. The primary tag 302 may be configured to identify the secondary tag 304 to be associated with the primary tag 302 if the unique secondary tag identification code matches the secondary tag identifier.

Various embodiments relate to an identification system.

Various embodiments relate to a system for identifying an infant by using active identification tags on mothers, infants, and baby cots. It provides for mother-infant matching and cot-infant matching for both single and multiple births; monitoring of the location, movement, and status of the tags; detection of tampering and unauthorized removal of infant tags; and organizing of tags. The system may be an identification system.

FIG. 4A shows a schematic 400*a* of a system for identifying a human or an animal according to various embodiments. The system may include a primary tag 402 and a secondary tag 404. The primary tag 402 may be configured to send a first tag-to-tag signal 406. The secondary tag 404 may be configured to receive the first tag-to-tag signal 406. The secondary tag 404 may be further configured to send a second tag-to-tag signal 408 upon receiving the first tag-to-tag signal 406. The second tag-to-tag signal 408 may include a unique secondary tag identification code. The primary tag 402 may be further configured to store a secondary tag identifier and receive the second tag-to-tag signal 408. The primary tag 402 may be further configured to identify the secondary tag 404 as a correct secondary tag associated with the primary tag 402 if the unique secondary tag identification code in the second tag-to-tag signal 408 matches the secondary tag identifier stored in the primary tag 402.

In various embodiments, the first tag-to-tag signal 406 may include a unique primary tag identification code.

In various embodiments, the secondary tag 404 may include a skin side configured to be positioned over the skin of a human or an animal. The secondary tag 404 may be further configured to send the second tag-to-tag signal 408 if the skin side of the secondary tag 404 is within a predetermined distance from the skin of a human or an animal. Accordingly, the secondary tag 404 may be configured not to send the second tag-to-tag signal 408 if the skin side of the secondary tag 404 falls outside the predetermined distance from the skin of a human or an animal.

In various embodiments, the secondary tag 404 may be configured to store a primary tag identifier. The secondary tag 404 may be configured to identify a primary tag 402 as a correct primary tag associated with the secondary tag 404 if the unique primary tag identification code matches the primary tag identifier stored in the secondary tag 404. Storing the primary tag identifier may provide an option for the secondary tag 404 to use the primary tag identifier for deciding how to respond to the primary tag 402 when the secondary tag receives the first tag-to-tag signal 406. For example, the secondary tag 404 may be configured in such a way that if, within a short period, the secondary tag 404 repeatedly receives first tag-to-tag signals 406 from the same associated primary tag 404 (identified by comparing the primary tag identifier with the unique primary tag identification code in the first tag-to-tag signals 406), the secondary tag 404 may not respond to every first tag-to-tag signal 406 but may respond only selectively, for example, at predetermined intervals or after every predetermined number of times the secondary tag 404 receives the first tag-to-tag signal 406 from the associated primary tag 402, to conserve the battery power of the secondary tag 404.

In various embodiments, the secondary tag 404 may include two opposing electrical terminals. The secondary tag 404 may also include an electrically conductive strap configured to electrically connect the two opposing electrical terminals. The secondary tag 404 may be configured to send the second tag-to-tag signal 408 upon the secondary tag receiving the first tag-to-tag signal 406 if the two opposing electrical terminals are electrically connected. Accordingly, the secondary tag 404 may be configured not to send the second tag-to-tag signal 408 upon the secondary tag receiving the first tag-to-tag signal 406 if the two opposing electrical terminals are electrically disconnected.

In various embodiments, the primary tag 402 may include a switch 412. The primary tag 402 may be configured to send the first tag-to-tag signal 406 by manual activation of the switch 412. The switch 412 may be a momentary on-off switch. The secondary tag 404 may be further configured to send a second tag-to-tag signal 408 upon receiving the first tag-to-tag signal 406. The switch 412 may enable a person, such as a mother or guardian of an infant, to verify, on an on-demand basis, whether a secondary tag 404 is a correct secondary tag associated with the primary tag 402. For instance, the switch 402 enables a mother or a guardian to verify, on an on-demand basis, whether the infant the mother or the guardian is carrying is the correct infant. The switch 402 may also enable the mother or the guardian to verify, on an on-demand basis, whether an infant in a cot is the correct baby for the cot.

The primary tag 402 may be further configured to send the first tag-to-tag signal 406 at preset intervals.

The system may include a tag configuration device. The preset intervals may be configurable by the tag configuration device. The preset intervals may range from 1 second to 10 seconds. Other preset intervals may be used, depending on the design, the application, and user requirements.

The primary tag 402 may be configured to give a first visual alert if the unique secondary tag identification code in the second tag-to-tag signal 408 matches the secondary tag identifier stored in the primary tag 402. The primary tag 402 may be configured to give additionally a first audio alert if a time lapse exceeds a preset duration. The time lapse may be measured from the time at which the unique secondary tag identification code in the previous second tag-to-tag signal matches the secondary tag identifier stored in the primary tag 402 to the time at which the unique secondary tag identification code in the second tag-to-tag signal 408 matches the secondary tag identifier stored in the primary tag 402.

In various embodiments, the primary tag 402 may be configured to send a matching information signal 414 if the unique secondary tag identification code in the second tag-to-tag signal 408 matches the secondary tag identifier stored in the primary tag 402 and if a time lapse exceeds a preset duration, the time lapse being measured from the time at which the unique secondary tag identification code in the previous second tag-to-tag signal matches the secondary tag identifier stored in the primary tag 402 to the time at which the unique secondary tag identification code in the second tag-to-tag signal 408 matches the secondary tag identifier stored in the primary tag 402 In various embodiments, the matching information signal 414 may include the unique primary tag identification code and other information including the location and battery level of the primary tag 402. The matching information signal 414 may include information indicating a match. In various embodiments the matching information signal 414 may be a long range signal. The matching information signal 414 may be in the range of 868 MHz to 928 MHz. However, other frequencies that fall outside of the range of 868 MHz to 928 MHz may be used. The frequency of the matching information signal may be subjected to the frequency allocation rules in which the tags are used.

The preset time duration may be configured by the tag configuration device. The preset time duration may range from 10 seconds to 10 minutes. Other preset time durations may be used, depending on the design, the application and user requirements.

In various embodiments, the primary tag 402 may be further configured to give a second audio alert and give a second visual alert if the unique secondary tag identification code in the second tag-to-tag signal 408 does not match the secondary tag identifier stored in the primary tag 402. The second audio alert may be different from the first audio alert and the second visual alert is different from the first visual alert.

The first audio alert may be a first melody. The first visual alert may be a green blinking light. The second audio alert may be a second melody. The second visual alert may be a red blinking light. The primary tag 402 may include an indicator light 410 for display the first visual alert and/or the second visual alert.

In various embodiments, the primary tag 402 may be further configured to send a mismatch information signal 416 if the unique secondary tag identification code in the second tag-to-tag signal 408 does not match the secondary tag identifier stored in the primary tag 402. The mismatch information signal 416 may include information indicating a mismatch. In various embodiments, mismatch information signal 416 may be a long range signal. The mismatch information signal 416 may be in the range of 868 MHz to 928 MHz. However, other frequencies that fall outside of the range of 868 MHz to 928 MHz may be used. The frequency of the mismatch information signal 416 may be subjected to the frequency allocation rules in which the tags are used.

In various embodiments, the secondary tag 404 may include two opposing electrical terminals. The secondary tag 404 may also include an electrically conductive strap configured to electrically connect the two opposing electrical terminals. The secondary tag 404 may be configured to send a connection information signal 418 if the two opposing electrical terminals are electrically connected. The connection information signal may include the unique secondary tag identification code and other information including the location and battery level of the secondary tag. The connection information signal 418 may include information indicating that the two opposing terminals are electrically connected. The secondary tag 404 may be configured to send the connection information signal 418 at preset intervals. In various embodiments, the connection information signal 418 may be a long range signal. The connection information signal 418 may be in the range of 868 MHz to 928 MHz. However, other frequencies that fall outside of the range of 868 MHz to 928 MHz may be used. The frequency of the connection information signal 418 may be subjected to the frequency allocation rules in which the tags are used.

The electrical conductive strap may have an electrical resistance that varies as the strap is stretched. The electrical resistance of the strap may be changed due to tampering of the strap. The secondary tag may be configured to send an information signal including information indicating that the strap may have been or might have been tampered with when the change in electrical resistance exceeds a preset threshold.

In various embodiments, the secondary tag 404 may include two opposing electrical terminals. The secondary tag 404 may also include an electrically conductive strap configured to electrically connect the two opposing electrical terminals. The secondary tag 404 may be configured to send a disconnection information signal 420 if the two opposing electrical terminals are electrically disconnected. The secondary tag 404 may be configured to send the disconnection information signal 420 at preset intervals for a preset surveillance period after the two opposing electrical terminals are electrically disconnected. Send the disconnection information signal 420 at preset intervals for the preset surveillance period may limit the period in which the secondary tag 404 is active and may help to conserve the battery power of the secondary tag 404. The disconnection information signal 420 may include information indicating the strap has been severed. In various embodiments, the secondary tag 494 may be configured to send the disconnection information signal immediately after the two opposing electrical terminals are electrically disconnected. In various embodiments, the disconnection information signal 420 may be a long range signal. The disconnection information signal 420 may be in the range of 868 MHz to 928 MHz. However, other frequencies that fall outside of the range of 868 MHz to 928 MHz may be used. The frequency of the disconnection information signal 420 may be subjected to the frequency allocation rules in which the tags are used.

The preset intervals may be configured by the tag configuration device. The preset surveillance period may be configured by the tag configuration device. The preset intervals may range from 5 seconds to 1 minute. The preset surveillance period may range from 1 minute to 10 minutes. Other ranges may be used, depending on the design, the application and user requirements.

In various embodiments, the secondary tag 404 may be configured to send the second tag-to-tag signal 408 upon the secondary tag 404 receiving the first tag-to-tag signal 406 if a time lapse exceeds a preset duration. The time lapse may be measured from the time at which the unique primary tag identification code in the previous first tag-to-tag signal 406 matches the primary tag identifer stored in the secondary tag 404 to the time at which the unique primary tag identification code in the first tag-to-tag signal 406 matches the primary tag identifier stored in the secondary tag 404.

The secondary tag 404 may not always respond with a second tag-to-tag signal 408 for every matching first tag-to-tag signal 406 the secondary tag 404 receives. For instance in a cot-infant system, it may not be required or desirable for the cot tag (i.e. the primary tag) 402 to keep giving audio or visual alerts, considering that an infant is likely to stay in the cot for extended periods. Having the secondary tag 404 configured to send the second tag-to-tag signal 408 upon the secondary tag 404 receiving the first tag-to-tag signal 406 if a time lapse exceeds a preset duration may help conserve the battery power of both the primary tag or cot tag 402 and the secondary tag or infant tag 404. The secondary tag or infant tag 404 may be configured to send the second tag-to-tag signal 408 consecutively for multiple times, e.g. two or three times, and not just once within a time interval (e.g. 3 minutes), to reduce the chances of the primary tag or cot tag 402 not receiving the second tag-to-tag signal 408 because of temporary physical obstacles between the primary or cot tag 402 and the secondary or infant tag 404.

The preset duration may be configurable by the tag configuration device. The preset duration may range from 10 seconds to 10 minutes. Other ranges may be used, depending on the design, the application, and user requirements.

In various embodiments, a transmission range of the first tag-to-tag signal 406 may be configured by the tag configuration device. In various embodiments, a transmission range of the second tag-to-tag signal 408 may be configured by the tag configuration device. In various embodiments, the first tag-to-tag signal 406 and/or the second tag-to-tag signal 408 may be short range signals.

In various embodiments, the maximum transmission range of the first tag-to-tag signal 406 and the maximum transmission range of the second tag-to-tag signal 408 for a system in which the primary tag 402 is intended to be worn on a mother or guardian may be longer than those for a system in which the primary tag 402 is intended to be attached to a cot. The transmission ranges of the first tag-to-tag signal 406 and the second tag-to-tag signals 408 in a cot-infant tag system may be made slightly shorter than the transmission ranges of the first tag-to-tag signal 406 and the second tag-to-tag signals 408 in a mother-infant tag system. A shorter transmission range for cot-infant tag systems may help to reduce the chances of cot tag and infant tag signals crossing from one cot to another, considering that cots in a maternity ward may be placed right next to each other.

In various embodiments, the maximum transmission range of the first tag-to-tag signal 406 and the maximum transmission range of the second tag-to-tag signals 408 may be approximately 40 centimeters for a system in which the primary tag 402 is intended to be worn on a mother or guardian and 36 centimeters for a system in which the primary tag 402 is intended to be attached to a cot. The transmission range of the first tag-to-tag signal 406 and the transmission range of the second tag-to-tag signal 408 may be configurable by the tag configuration device.

In various embodiments, the connection information signal 418 may be a long range signal. In various embodiments, the disconnection information signal 420 may also be a long range signal. In various embodiments, the matching information signal 414 may be a long range signal. In various embodiments, the mismatch information signal 416 may also be a long range signal. In various embodiments, the connection information signal 418 may have a transmission range of 10 m to 25 m. The disconnection information signal 420 may also have a transmission range 10 m to 25 m. In various embodiments, the matching information signal 414 may have a transmission range of 10 m to 25 m. The mismatch information signal 416 may also have a transmission range 10 m to 25 m. Other ranges may also be used, depending on the design, the application, and user requirements.

In various embodiments, the system may include a plurality of secondary tags. The primary tag 402 may be configured to store a plurality of secondary tag identifiers and receive a second tag-to-tag signal from each secondary tag of the plurality of secondary tags. The primary tag 402 may be further configured to identify a secondary tag (e.g. 404) as a correct secondary tag associated with the primary tag 402 if the unique secondary tag identification code in the second tag-to-tag signal (e.g. 406) sent by the secondary tag (e.g. 404) matches any one of the secondary tag identifiers stored in the primary tag 402.

The system may include at least one receiver 422. The at least one receiver 422 may be configured to receive the matching information signal 414 and/or mismatch information signal 416 sent by the primary tag 402. The at least one receiver 422 may additionally or alternatively be configured to receive the connection information signal 418 and/or disconnection information signal 420 sent by the secondary tag 404.

The system may further include a computer system 424. The computer system 424 may be configured to receive, store, and process the matching information signal 414 and/or the mismatch information signal 416 and/or the connection information signal 418 and/or the disconnection information signal 420 received by the at least one receiver 422, and on the basis of the signals, issue alerts regarding the status of the primary tag 402 and/or the secondary tag 404.

The at least one receiver 422 and the computer system 424 may form a complete location and status tracking system. The location and status tracking system may be part of a larger system such as a hospital's nurse call system or a security system. In one instance, the at least one receivers 422 may be installed in places where mothers, the infants and cots are expected to reside. The at least one receiver 422 may also be installed in strategic exit locations to monitor the movement of the secondary or infant tags for the purpose of detecting infant abduction and/or unauthorized movement of infants. The at least one receiver 422 may be configured to give an audible alarm, a visual alarm or both when the at least one receiver 422 receives the matching information signal and/or mismatch information signal sent by the primary tag 402 and/or the connection information signal and/or disconnection information signal sent by the secondary tag 404.

In various embodiments, the computer system 424 may issue an alert if the computer system 424 does not receive the connection information signal 418 and/or the disconnection information signal 420 for a preset nondetection period. Such an alert may be used to trigger personnel, e.g. hospital staff, to check the secondary tag 404 that is supposed to send the connection information signal 418 and/or the disconnection information signal 420, as well as the wearer of the secondary tag 404.

The preset nondetection period may be configurable. Configuration of the preset nondetection period may be accomplished through the application software of the computer system 424. The preset nondetection period may range from 10 seconds to 10 minutes. Other ranges may be used, depending on the design, the application, and the user requirements.

The system may further include a location beacon 426. The location beacon 426 may be configured to send a first beacon signal 428. The first beacon signal 428 may include information indicating the location of the location beacon 426. The primary tag 402 may be configured to receive the first beacon signal 428 and send a primary response signal in response to the first beacon signal 428. The location beacon 426 may be configured to receive the primary response signal. The primary response signal may indicate the location of the primary tag 402.

The location beacon 426 may be configured to send a second beacon signal 430. The second beacon signal 430 may include information indicating the location of the location beacon 426. The secondary tag 404 may be configured to receive second beacon signal 430 and send a secondary response signal in response to the second beacon signal 430. The location beacon 426 may be configured to receive the secondary response signal. The secondary response signal may indicate the location of the secondary tag 404.

The location beacon 426 may allow for the registering and updating of the mother tag, the cot tag, and/or the infant tag. The location beacon 426 may be installed inside of a room simply to provide a room location for the tags. The location beacon 426 may also be installed at strategic exit locations to provide the location of these exit locations for the purpose of detecting infant abduction and/or unauthorized movement of infants.

The system may further include a tag configuration device. The tag configuration device may be configured to set parameters for the primary tag 402 and/or secondary tag 404. The parameters may be selected from a group including the intervals at which a signal is sent and/or the transmission range of the signal. The signal may be, for instance, the first tag-to-tag signal, the second tag-to-tag signal, the connection information signal, the disconnection information signal, the matching information signal, the mismatch information signal and/or any other signals sent by the primary tag 402 or the secondary tag 404. The group may further include the preset durations, the predetermined distance of the skin side of the secondary tag from the skin, the sensitivity of the secondary tag in detecting the skin, and the threshold for the change in electrical resistance of the strap.

In various embodiments, the primary tag 402 may include a built-in transmitter. The primary tag 402 may further include a detachable transmitter. The primary tag 402 may be further configured to send the first tag-to-tag signal 406 by the detachable transmitter if the detachable transmitter is attached to the primary tag 402. The primary tag 402 may be configured to send the first tag-to-tag signal 406 by the built-in transmitter if the detachable transmitter is detached from the primary tag 402.

In various embodiments, the unique secondary tag identification code in the second tag-to-tag signal 408 may match the secondary tag identifier stored in the primary tag 402 if the unique secondary tag identification code and the secondary tag identifier include a common string of characters.

In various embodiments, the unique primary tag identification code in the first tag-to-tag signal 406 may match the primary tag identifier stored in the secondary tag 404 if the unique primary tag identification code and the primary tag identifier include a common string of characters.

The unique secondary tag identification code and the unique primary tag identification code may or may not include a common string of characters.

Tables 1 to 4 illustrate the use of identification codes and identifiers.

TABLE 1

First examples of identification codes and identifiers for mother-infant and cot-infant tag systems (one-to-one matching of primary and secondary tags).

| Mother/cot | Mother/cot tag identification code | Mother/cot tag identifier stored by infant tag | Infant tag identification code | Infant tag identifier stored by mother/cot tag |
|---|---|---|---|---|
| A | 67001234 | 67001234 | 61001234 | 61001234 |
| B | 67005678 | 67005678 | 61005678 | 61005678 |

TABLE 2

Second examples of identification codes and identifiers for mother-infant and cot-infant tag systems (one-to-one matching of primary and secondary tags).

| Mother/cot | Mother/cot tag identification code | Mother/cot tag identifier stored by infant tag | Infant tag identification code | Infant tag identifier stored by mother/cot tag |
|---|---|---|---|---|
| A | 67001234 | 67001234 | 61001234 | 001234 |
| B | 67005678 | 67005678 | 61005678 | 5678 |

TABLE 3

First examples of identification codes for mothers
with four babies (one-to-four matching).

| Mother | Mother tag identification code | Mother tag identifier stored by infant tag | Infant tag identification code | Infant tag identifier stored by mother tag |
|---|---|---|---|---|
| C | 6700F 001 | 6700F 001 | 6100F 001 | 6100F 001 |
|   |           | 6700F 001 | 6100F 002 | 6100F 002 |
|   |           | 6700F 001 | 6100F 003 | 6100F 003 |
|   |           | 6700F 001 | 6100F 004 | 6100F 004 |
| D | 6700F 006 | 6700F 006 | 6100F 006 | 6100F 006 |
|   |           | 6700F 006 | 6100F 007 | 6100F 007 |
|   |           | 6700F 006 | 6100F 008 | 6100F 008 |
|   |           | 6700F 006 | 6100F 009 | 6100F 009 |

TABLE 4

Second examples of identification codes for mothers
with four babies (one-to-four matching).

| Mother | Mother tag identification code | Mother tag identifier stored by infant tag | Infant tag identification code | Infant tag identifier stored by mother tag |
|---|---|---|---|---|
| C | 6700F 001 | 6700F 001 | 6100F 001 | 00F 001 |
|   |           | 6700F 001 | 6100F 002 | 00F 002 |
|   |           | 6700F 001 | 6100F 003 | 00F 003 |
|   |           | 6700F 001 | 6100F 004 | 00F 004 |
| D | 6700F 006 | 6700F 006 | 6100F 006 | F 006 |
|   |           | 6700F 006 | 6100F 007 | F 007 |
|   |           | 6700F 006 | 6100F 008 | F 008 |
|   |           | 6700F 006 | 6100F 009 | F 009 |

In Table 1, the mother/cot tag 402 stores the full infant tag identification code as the infant tag identifier (secondary tag identifier). In Table 2, the mother/cot tag 402 stores only part of the infant tag identification code as the infant tag identifier. In both tables, the infant tag identification code (secondary tag identification code) and infant tag identifier (secondary tag identifier) for each mother share a common string of characters, and the mother/cot tag identification code and mother/cot tag identifier for each mother also share a common string of characters. It should be emphasized that a cot tag can be matched with only one infant tag.

In Table 3, each mother tag 402 stores the full infant tag identification code for each infant as the infant tag identifier for that infant. In Table 4, each mother tag 402 stores only part of the infant tag identification code as the infant tag identifier. In both tables, the infant tag identification code and infant tag identifier for each mother share a common string of characters, and the mother tag identification code and mother tag identifier for each mother also share a common string of characters.

In various instances, the unique secondary tag identification code in the second tag-to-tag signal 408 may match the secondary tag identifier stored in the primary tag 402 if the unique secondary tag identification code and the secondary tag identifier include a minimum number of characters that are common. The minimum number of characters may be predefined. In various other embodiments, the unique secondary tag identification code in the second tag-to-tag signal 408 may match the secondary tag identifier stored in the primary tag 402 if the characters in predefined positions in a string of characters are the same.

Similarly, the unique primary tag identification code in the first tag-to-tag signal 406 may match the primary tag identifier stored in the secondary tag 404 if the unique primary tag identification code and the primary tag identifier include a minimum number of characters that are common. The minimum number of characters may be predefined.

In various other embodiments, the unique secondary tag identification code in the second tag-to-tag signal 408 may match the secondary tag identifier stored in the primary tag 402 if the characters in predefined positions in a string of characters are the same.

Similarly, the unique primary tag identification code in the first tag-to-tag signal 406 may match the primary tag identifier stored in the secondary tag 404 if the characters in predefined positions in a string of characters are the same.

In various other embodiments, the unique secondary tag identification code in the second tag-to-tag signal 408 may match the secondary tag identifier stored in the primary tag 402 if the unique secondary tag identification code and the secondary tag identifier are the same. Accordingly, the unique secondary tag identification code in the second tag-to-tag signal 408 may not match the secondary tag identifier stored in the primary tag 402 if the unique secondary tag identification code and the secondary tag identifier are different.

Similarly, the unique primary tag identification code in the first tag-to-tag signal 406 may match the primary tag identifier stored in the secondary tag 404 if the unique primary tag identification code and the primary tag identifier are the same. Accordingly, the unique primary tag identification code in the first tag-to-tag signal 406 may not match the primary tag identifier stored in the secondary tag 404 if the unique primary tag identification code and the primary tag identifier are different.

In various alternate embodiments, the unique secondary tag identification code in the second tag-to-tag signal 408 may match the secondary tag identifier stored in the primary tag 402 if the unique secondary tag identification code and the secondary tag identification satisfy a predetermined condition or satisfy a predetermined relation. For instance, the primary tag 402 may be configured such the unique secondary tag identification code in the second tag-to-tag signal 408 matches the secondary tag identifier stored in the primary tag 402 if the last four digits of the unique secondary tag identification code and the last four digits of the secondary tag identifier add up to a predefined number, e.g. 10,000. In another instance, the primary tag 402 may be configured such that the secondary tag identifier stored in the primary tag 402 is linked with one or more predetermined secondary tag identification codes and a unique secondary tag identification code in the second tag-to-tag signal may match the secondary tag identifier only if the unique secondary tag identification code is one of the one or more predetermined secondary tag identification codes. Accordingly, the unique secondary tag identification code in the second tag-to-tag signal may not match the secondary tag identifier stored in the primary tag 402 if the unique secondary tag identification code and the secondary tag identification does not satisfy the predetermined condition or does not satisfy a predetermined relation.

Similarly, the unique primary tag identification code in the first tag-to-tag signal 406 may match the primary tag identifier stored in the secondary tag 404 if the unique primary tag identification code and the primary tag identification satisfy a predetermined condition or satisfy a predetermined relation.

In various embodiments, the primary tag 402 may be labeled with the unique primary tag identification code such that the unique primary tag identification code is visually recognizable and readable. In various embodiments, the secondary tag 404 may be labeled with the unique secondary tag identification code such that the unique secondary tag identification code is visually recognizable and readable.

In various embodiments, the secondary tag 404 may further include an indication light 428.

FIG. 4B shows a schematic 400b of a primary tag storage bracket 450 according to various embodiments and a secondary tag storage bracket 452 according to various embodiments. In various embodiments, the system may include a primary tag storage bracket 450 for storing a primary tag 454. The system may further include a secondary storage bracket 452 for storing the secondary tag 456.

The primary tag storage bracket 450 may be configured such that it turns off the primary tag's capability to send or receive any signal whenever the primary tag 454 is placed in the primary tag storage bracket 452 for a preset period.

The preset period may be configurable by the tag configuration device. The preset period may range from 1 second to 10 seconds. Other ranges may be used, depending on the design, the application, and user requirements.

In various embodiments, the secondary tag 404 may be configured to send an information signal if the skin side of the secondary tag 404 is within a predetermined distance from the skin. For example, when a secondary tag/infant tag 404 is strapped to an infant for extended periods of time, the strap may become too tight for the infant as the infant grows or becomes too loose if the infant loses weight. Having the secondary tag 404 configured to send the information signal if the skin side of the secondary tag 404 is within the predetermined distance from the skin may circumvent the problem of the strap being too tight or too loose for the infant.

It may be understood that a device, such as a tag, referred to in one figure may be the same tag referred to in another figure. The primary tag in FIG. 4B may be a primary tag shown in FIG. 1A, FIG. 1B, or FIG. 4A. The secondary tag in FIG. 4B may be a secondary tag shown in FIG. 2A, FIG. 2B, or FIG. 4A.

FIG. 5 shows a schematic 500 of a method of identifying a human or an animal according to various embodiments. The method may include, in 502, sending a first tag-to-tag signal from a primary tag to a secondary tag. The method may include, in 504, receiving the first tag-to-tag signal by the secondary tag. The method may further include, in 506, sending a second tag-to-tag signal by the secondary tag, upon receiving the first tag-to-tag signal. The second tag-to-tag signal may include a unique secondary tag identification code. The method may also include, in 508, receiving the second tag-to-tag signal by the primary tag. The method may further include, in 510, identifying the secondary tag, by the primary tag, as a correct secondary tag associated with the primary tag if the unique secondary tag identification code in the second tag-to-tag signal matches a secondary tag identifier stored in the primary tag.

In other words, the method may include transmitting a first tag-to-tag signal from a primary tag to a secondary tag. The method may also include transmitting a second tag-to-tag signal from the secondary tag to the primary tag in response to the first tag-to-tag signal. The second tag-to-tag signal may include a unique secondary tag identification code. The method may further include comparing the unique secondary tag identification code with a secondary tag identifier stored in the primary tag and identifying the secondary tag as a correct secondary tag associated with the primary tag if the unique secondary tag identification code matches the secondary tag identifier.

Various embodiments relate to a method of using active tags. Various embodiments of using a tag may include controlling the tag.

Various embodiments relate to a method of identifying an infant by using active identification tags on mothers, infants, and baby cots. It provides for mother-infant matching and cot-infant matching for both single and multiple births; monitoring of the location, movement, and status of the tags; detection of tampering and unauthorized removal of infant tags; and organizing of tags.

FIG. 6 shows a schematic 600 of a method of controlling a primary tag for communication with a secondary tag according to various embodiments. The method may include, in 602, storing a secondary tag identifier. The method may include, in 604, receiving a second tag-to-tag signal from the secondary tag. The second tag-to-tag signal may include a unique secondary tag identification code. The method may also include, in 606, identifying the secondary tag as a correct secondary tag associated with the primary tag if the unique secondary tag identification code in the second tag-to-tag signal matches the secondary tag identifier.

In other words, the method may include storing by the primary tag, a secondary tag identifier. The method may also include receiving, by the primary tag, a second tag-to tag signal from the secondary tag. The second tag-to-tag signal may include a unique secondary tag identification code. The method may further include comparing by the primary tag, the unique secondary tag identification code with the secondary tag identifier and identifying the secondary tag as a correct secondary tag associated with the primary tag if the unique secondary tag identification code in the second tag-to-tag signal matches the secondary tag identifier.

FIG. 7 shows schematic 700 of a method of controlling a secondary tag for communication with a primary tag according to various embodiments. The method may include, in 702, receiving a first tag-to-tag signal from the primary tag. The first tag-to-tag signal may include a unique primary tag identification code. The method may include, in 704, sending a second tag-to-tag signal upon receiving the first tag-to-tag signal. The second tag-to-tag signal may include a unique secondary tag identification code.

In other words, the method may include receiving, by the secondary tag, receiving a first tag-to-tag signal from the primary tag. The first tag-to-tag signal may include a unique primary tag identification code. The method may also include sending, by the secondary tag, a second tag-to-tag signal after receiving the tag-to-tag signal. The second tag-to-tag signal may include a unique secondary tag identification code.

Methods described herein may further contain analogous features of any device or system described herein.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A primary tag for communication with a secondary tag, the primary tag comprising:
   a memory circuit configured to store a secondary tag identifier;
   a receiver circuit configured to receive a second tag-to-tag signal from the secondary tag, the second tag-to-tag signal comprising a unique secondary tag identification code;
   a processor circuit configured to identify the secondary tag as a correct secondary tag associated with the primary tag if the unique secondary tag identification code in the second tag-to-tag signal matches the secondary tag identifier stored in the memory circuit;

a first transmitter circuit configured to send a first tag-to-tag signal, the first tag-to-tag signal comprising a unique primary tag identification code; and a second transmitter circuit configured to send an information signal, the information signal comprising the unique primary tag identification code and other information including the location and battery level of the primary tag.

2. The primary tag of claim 1, further comprising:

a receiving portion configured to receive a detachable transmitter, wherein the first transmitter circuit comprises a built-in transmitter, and wherein the primary tag is configured to send the first tag-to-tag signal by the detachable transmitter if the detachable transmitter is attached to the primary tag and configured to send the first tag-to-tag signal by the built-in transmitter if the detachable transmitter is detached from the primary tag.

3. The primary tag of claim 1, further comprising:

a switch, wherein the first transmitter circuit is configured to send the first tag-to-tag signal by manual activation of the switch.

4. The primary tag of claim 1, wherein the first transmitter circuit is further configured to send the first tag-to-tag signal at preset intervals.

5. The primary tag of claim 1, further comprising a display circuit configured to give a first visual alert if the unique secondary tag identification code in the second tag-to-tag signal matches the secondary tag identifier stored in the memory circuit; and an alarm circuit configured to give additionally a first audio alert if a time lapse exceeds a preset duration, the time lapse being measured from the time at which the unique secondary tag identification code in the previous second tag-to-tag signal matches the secondary tag identifier stored in the memory circuit to the time at which the unique secondary tag identification code in the second tag-to-tag signal matches the secondary tag identifier stored in the memory circuit.

6. The primary tag of claim 1, wherein the second transmitter circuit is configured to send a matching information signal if the unique secondary tag identification code in the second tag-to-tag signal matches the secondary tag identifier stored in the memory circuit and if a time lapse exceeds a preset duration, the time lapse being measured from the time at which the unique secondary tag identification code in the previous second tag-to-tag signal matches the secondary tag identifier stored in the memory circuit to the time at which the unique secondary tag identification code in the second tag-to-tag signal matches the secondary tag identifier stored in the memory circuit; and wherein the matching information signal comprises the unique primary tag identification code and other information including the location and battery level of the primary tag.

7. The primary tag of claim 5, wherein the alarm circuit is further configured to give a second audio alert and the display circuit is further configured to give a second visual alert if the unique secondary tag identification code in the second tag-to-tag signal does not match the secondary tag identifier stored in the memory circuit, and wherein the second audio alert is different from the first audio alert and the second visual alert is different from the first visual alert.

8. The primary tag of claim 6, wherein the second transmitter circuit is further configured to send a mismatch information signal if the unique secondary tag identification code in the second tag-to-tag signal does not match the secondary tag identifier stored in the memory circuit, and wherein the mismatch information signal comprises information indicating a mismatch.

9. The primary tag of claim 1, wherein the first transmitter circuit is configured to send the first tag-to-tag signal having a first maximum transmission range when the primary tag is intended to be worn on a person and configured to send the first tag-to-tag signal having a second maximum transmission range when the primary tag is intended to be attached to a cot, wherein the receiving circuit is configured to receive the second tag-to-tag signal having a first maximum reception range when the primary tag is intended to be worn on a person and configured to receive the second tag-to-tag signal having a second maximum reception range when the primary tag is to intended be attached to a cot, wherein the first maximum transmission range is longer than the second maximum transmission range, and wherein the first maximum reception range is longer than the second maximum reception range.

10. The primary tag of claim 8, wherein the matching information signal and the mismatch information signal are configured to be received by at least one receiver connected to a computer system; and wherein information comprised in the matching information signal and the mismatch information signal is configured to be received, stored, and processed by the computer system.

11. The primary tag of claim 1, wherein the receiver circuit is configured to receive a beacon signal from a location beacon, wherein the second transmitter circuit is configured to send a primary tag response information signal in response to the beacon signal received by the receiver circuit, and wherein the primary tag response information signal comprises information indicating the location of the primary tag.

12. The primary tag of claim 1, wherein at least one parameter of the primary tag is configured by a tag configuration device, the at least one parameter being selected from a group comprising the intervals at which the first tag-to-tag signal is sent and a transmission range of the first tag-to-tag signal.

13. The primary tag of claim 1, wherein the unique secondary tag identification code in the second tag-to-tag signal matches the secondary tag identifier stored in the memory circuit if the unique secondary tag identification code and the secondary tag identifier comprise a common string of characters.

14. The primary tag of claim 1, wherein the primary tag is labeled with the unique primary tag identification code such that the unique primary tag identification code is visually recognizable and readable.

15. The primary tag of claim 1,
wherein the primary tag is configured to be stored in a primary storage bracket, and
wherein the primary tag's capability to send or receive any signal is turned off by the primary storage bracket after the primary tag is placed in the primary tag storage bracket for a preset period.

16. The primary tag of claim 1,
wherein the memory circuit is further configured to store a plurality of secondary tag identifiers, and
wherein the processor circuit is further configured to identify the secondary tag as a correct secondary tag associated with the primary tag if the unique secondary tag identification code in the second tag-to-tag signal matches any one of the secondary tag identifiers stored in the memory circuit.

17. A secondary tag for communication with a primary tag, the secondary tag comprising:
a receiver circuit configured to receive a first tag-to-tag signal from the primary tag, the first tag-to-tag signal comprising a unique primary tag identification code;
a first transmitter circuit configured to send a second tag-to-tag signal upon the receiver circuit receiving the first tag-to-tag signal, the second tag-to-tag signal comprising a unique secondary tag identification code;
a skin side configured to be positioned over the skin of a human or an animal; and
a skin detection circuit configured to detect whether the skin side is within a predetermined distance from the skin of a human or an animal;
wherein the first transmitter circuit is further configured to send the second tag-to-tag signal upon the receiver circuit receiving the first tag-to-tag signal if the skin detection circuit determines that the skin side of the secondary tag is within a predetermined distance from the skin of a human or an animal.

18. The secondary tag of claim 17, further comprising
a memory circuit configured to store a primary tag identifier, and
a processor circuit configured to identify the primary tag as a correct primary tag associated with the secondary tag if the unique primary tag identification code matches the primary tag identifier stored in the memory circuit.

19. The secondary tag of claim 17, further comprising:
two opposing electrical terminals,
an electrically conductive strap configured to electrically connect the two opposing electrical terminals, and
a detection circuit configured to detect whether the two opposing electrical terminals are electrically connected by the electrically conductive strap;
wherein the first transmitter circuit is configured to send the second tag-to-tag signal tag upon the receiver circuit receiving the first tag-to-tag signal if the detection circuit determines that the two opposing electrical terminals are electrically connected.

20. The secondary tag of claim 17, further comprising:
a second transmitter circuit,
two opposing electrical terminals,
an electrically conductive strap configured to electrically connect the two opposing electrical terminals, and
a detection circuit configured to detect whether the two opposing electrical terminals are electrically connected by the electrically conductive strap;
wherein the second transmitter circuit is configured to send a connection information signal if the detection circuit determines that the two opposing electrical terminals are electrically connected, and
wherein the connection information signal comprises the unique secondary tag identification code and other information including the location and battery level of the secondary tag.

21. The secondary tag of claim 20,
wherein the secondary tag is configured to send the connection information signal at preset intervals.

22. The secondary tag of claim 17, further comprising:
a second transmitter circuit,
two opposing electrical terminals,
an electrically conductive strap configured to electrically connect the two opposing electrical terminals, and
a detection circuit configured to detect whether the two opposing electrical terminals are electrically connected by the electrically conductive strap;
wherein the second transmitter circuit is configured to send a disconnection information signal if the detection circuit determines that the two opposing electrical terminals are electrically disconnected,
wherein the second transmitter circuit is configured to send the disconnection information signal at preset intervals for a preset surveillance period after the detection circuit determines that the two opposing electrical terminals are electrically disconnected, and
wherein the disconnection information signal comprises information indicating the strap has been severed.

23. The secondary tag of claim 18,
wherein the first transmitter circuit is configured to send the second tag-to-tag signal upon the receiver circuit receiving the first tag-to-tag signal if the processor circuit determines that a time lapse exceeds a preset duration, the time lapse being measured from the time at which the unique primary tag identification code in the previous first tag-to-tag signal matches the primary tag identifier stored in the memory circuit to the time at which the unique primary tag identification code in the first tag-to-tag signal matches the primary tag identifier stored in the memory circuit.

24. The secondary tag of claim 20,
wherein the connection information signal is configured to be received by at least one receiver connected to a computer system; and
wherein information comprised in the connection information signal is configured to be received, stored, and processed by the computer system.

25. The secondary tag of claim 24,
wherein an alert is issued by the computer system if the computer system does not receive the connection information signal for a preset nondetection period.

26. The secondary tag of claim 22,
wherein the disconnection information signal is configured to be received by at least one receiver connected to a computer system; and
wherein information comprised in the disconnection information signal is configured to be received, stored, and processed by the computer system.

27. The secondary tag of claim 26,
wherein an alert is issued by the computer system if the computer system does not receive the disconnection information signal for a preset nondetection period.

28. The secondary tag of claim 17, further comprising
a second transmitter circuit,
wherein the receiver circuit is configured to receive a beacon signal from a location beacon, wherein the second transmitter circuit is configured to send a secondary tag response information signal in response to the beacon signal received by the receiver circuit, and wherein the secondary tag response information signal comprises information indicating the location of the secondary tag.

29. The secondary tag of claim 17, further comprising a second transmitter circuit, wherein the second transmitter circuit is configured to send an information signal, and wherein the information signal comprises the unique secondary tag identification code and other information including the location and battery level of the secondary tag.

30. The secondary tag of claim 17, wherein at least one parameter of the secondary tag is configured by a tag configuration device, the at least one parameter being selected from a group comprising the intervals at which the second tag-to-tag signal is sent and a transmission range of the second tag-to-tag signal.

31. The secondary tag of claim 18, wherein the unique primary tag identification code in the first tag-to-tag signal matches the primary tag identifier stored in the memory circuit if the unique primary tag identification code and the primary tag identifier comprise a common string of characters.

32. The secondary tag of claim 17, wherein the secondary tag is labeled with the unique secondary tag identification code such that the unique secondary tag identification code is visually recognizable and readable.

33. The secondary tag of claim 17, further comprising a second transmitter circuit, wherein the second transmitter circuit is configured to send an information signal if the skin detection circuit detects that the skin side of the secondary tag is within a predetermined distance from the skin.

34. The secondary tag of claim 17, wherein the secondary tag is configured to be stored in a secondary tag bracket.

35. A system for identifying a human or an animal, the system comprising:

a primary tag, a secondary tag, and a primary tag storage bracket for storing the primary tag;

wherein the primary tag is configured to send a first tag-to-tag signal;

wherein the secondary tag is configured to receive the first tag-to-tag signal;

wherein the secondary tag is further configured to send a second tag-to-tag signal upon receiving the first tag-to-tag signal, the second tag-to-tag signal comprising a unique secondary tag identification code;

wherein the primary tag is further configured to store a secondary tag identifier and receive the second tag-to-tag signal;

wherein the primary tag is further configured to identify the secondary tag as a correct secondary tag associated with the primary tag if the unique secondary tag identification code in the second tag-to-tag signal matches the secondary tag identifier stored in the primary tag; and wherein the primary tag storage bracket is configured such that it turns off the primary tag's capability to send or receive any signal whenever the primary tag is placed in the primary tag storage bracket for a preset period.

36. The system of claim 35, wherein the first tag-to-tag signal comprises a unique primary tag identification code.

37. The system of claim 35, wherein the system comprises a plurality of secondary tags, wherein the primary tag is configured to store a plurality of secondary tag identifiers and receive a second tag-to-tag signal from each secondary tag of the plurality of secondary tags, and wherein the primary tag is further configured to identify a secondary tag as a correct secondary tag associated with the primary tag if the unique secondary tag identification code in the second tag-to-tag signal sent by the secondary tag matches any one of the secondary tag identifiers stored in the primary tag.

38. The system of claim 35, wherein the secondary tag comprises a skin side configured to be positioned over the skin of a human or an animal, wherein the secondary tag is further configured to send the second tag-to-tag signal if the skin side of the secondary tag is within a predetermined distance from the skin of a human or an animal.

39. The system of claim 35, wherein the secondary tag further comprises two opposing electrical terminals, and an electrically conductive strap configured to electrically connect the two opposing electrical terminals;

wherein the secondary tag is configured to send a disconnection information signal if the two opposing electrical terminals are electrically disconnected, wherein the secondary tag is configured to send the disconnection information signal at preset intervals for a preset surveillance period after the two opposing electrical terminals are electrically disconnected, and wherein the disconnection information signal comprises information indicating the strap has been severed.

40. The system of claim 35, wherein the primary tag comprises a built-in transmitter and a detachable transmitter, wherein the primary tag is further configured to send the first tag-to-tag signal by the detachable transmitter if the detachable transmitter is attached to the primary tag and configured to send the first tag-to-tag signal by the built-in transmitter if the detachable transmitter is detached from the primary tag.

* * * * *